US009463076B2

(12) United States Patent
Yamashita et al.

(10) Patent No.: US 9,463,076 B2
(45) Date of Patent: Oct. 11, 2016

(54) DENTAL TREATING APPARATUS

(71) Applicant: J. Morita Manufacturing Corporation, Kyoto (JP)

(72) Inventors: Seiichiro Yamashita, Kyoto (JP); Kyoshi Tokunaga, Kyoto (JP); Naoki Katsuda, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 63 days.

(21) Appl. No.: 13/775,757

(22) Filed: Feb. 25, 2013

(65) Prior Publication Data
US 2013/0224677 A1 Aug. 29, 2013

(30) Foreign Application Priority Data

Feb. 24, 2012 (JP) ................................. 2012-038976

(51) Int. Cl.
*A61C 1/00* (2006.01)
*A61C 19/04* (2006.01)
(52) U.S. Cl.
CPC ............. *A61C 1/003* (2013.01); *A61C 19/042* (2013.01)
(58) Field of Classification Search
CPC ............................... A61C 1/186; A61C 1/003
USPC ............................................... 433/27, 98–99
See application file for complete search history.

(56) References Cited

U.S. PATENT DOCUMENTS

| | | | | |
|---|---|---|---|---|
| 3,578,745 A * | 5/1971 | Garnier | ................. | A61C 1/07 433/102 |
| 5,902,105 A * | 5/1999 | Uejima | ................. | A61C 5/025 433/27 |
| 5,980,248 A | 11/1999 | Kusakabe et al. | | |
| 6,293,795 B1 * | 9/2001 | Johnson | ............... | A61C 1/0015 433/102 |
| 7,476,101 B2 * | 1/2009 | McPherson et al. | ........... | 433/75 |
| 8,047,842 B2 * | 11/2011 | Johnson | ................. | A61C 5/023 206/369 |

(Continued)

FOREIGN PATENT DOCUMENTS

DE     10219648 A1    11/2002
JP      3264607 B2     3/2002

(Continued)

OTHER PUBLICATIONS

English abstract of Japanese Publication No. 3264607 published on Mar. 11, 2002, Espacenet database, 1 page.

(Continued)

*Primary Examiner* — Cris L Rodriguez
*Assistant Examiner* — Hao D Mai
(74) *Attorney, Agent, or Firm* — Osha Liang LLP

(57) ABSTRACT

The present invention is directed to a dental treating apparatus including: a hand piece; a power source (micro motor); a driving unit (motor driver); a driving state detecting unit (resistor for load detection, root canal length measuring circuit); and a controller. The hand piece drivably holds a cutting tool on a head unit. The power source drives the cutting tool. The driving unit drives the cutting tool with twist driving in which the normal rotation and the reverse rotation are repeated. The driving state detecting unit detects a driving state of the cutting tool. The controller changes at least one parameter of a rotation angle in the normal rotation, a rotation angle speed in the normal rotation, a rotation angle in the reverse rotation, and a rotation angle speed in the reverse rotation in accordance with the driving state of the cutting tool detected by the driving state detecting unit.

13 Claims, 11 Drawing Sheets

(56) References Cited

U.S. PATENT DOCUMENTS

| | | | |
|---|---|---|---|
| 9,017,076 B2* | 4/2015 | Danger | A61C 1/003 433/224 |
| 2002/0025504 A1* | 2/2002 | Satake | A61C 1/185 433/106 |
| 2002/0064756 A1* | 5/2002 | Pagnini | A61C 5/02 433/102 |
| 2002/0182564 A1* | 12/2002 | Katsuda | A61C 1/0015 433/98 |
| 2005/0042572 A1 | 2/2005 | Katsuda et al. | |
| 2011/0039229 A1* | 2/2011 | Senia | A61C 1/052 433/131 |
| 2012/0107766 A1* | 5/2012 | Borgschulte | A61C 1/003 433/102 |
| 2012/0122055 A1* | 5/2012 | Ramos | A61C 1/003 433/102 |
| 2012/0301840 A1* | 11/2012 | Poli | A61C 1/003 433/27 |
| 2013/0099710 A1* | 4/2013 | Okamoto | A61C 1/0015 318/434 |
| 2014/0134565 A1* | 5/2014 | Kunisada | A61C 1/0007 433/27 |
| 2014/0322669 A1* | 10/2014 | Kunisada | A61C 1/003 433/102 |
| 2015/0086937 A1* | 3/2015 | Katsuda | A61C 1/186 433/27 |
| 2015/0125807 A1* | 5/2015 | Shipley | A61B 17/1626 433/27 |
| 2015/0342702 A1* | 12/2015 | Borgschulte | A61C 5/02 433/27 |

FOREIGN PATENT DOCUMENTS

| | | | | |
|---|---|---|---|---|
| JP | 2003-504113 A | 2/2003 | | |
| JP | 3615209 B2 | 2/2005 | | |
| JP | 3676753 B2 | 7/2005 | | |
| JP | EP 2851034 A1 * | 3/2015 | | A61C 5/023 |
| WO | 2010/066337 A1 | 6/2010 | | |
| WO | 2010/109464 A2 | 9/2010 | | |

OTHER PUBLICATIONS

English abstract of Japanese Publication No. 3676753 published on Jul. 27, 2005, Espacenet database, 1 page.
English abstract of Japanese Publication No. 3615209 published on Feb. 2, 2005, Espacenet database, 1 page.
English abstract of Japanese Publication No. 2003504113 published on Feb. 4, 2003, Espacenet database, 1 page.
Office Action issued in counterpart German Patent Application No. 10 2013 002 509.5 dated Feb. 18, 2014 (11 pages).

* cited by examiner

FIG.9

|  | NORMAL ROTATION || REVERSE ROTATION ||
|  | ROTATION ANGLE | NUMBER OF ROTATIONS (ROTATION ANGLE SPEED) | ROTATION ANGLE | NUMBER OF ROTATIONS (ROTATION ANGLE SPEED) |
| --- | --- | --- | --- | --- |
| SETTING 1 | DECREASE | — | — | — |
| SETTING 2 | — | DECREASE | — | — |
| SETTING 3 | DECREASE | DECREASE | — | — |
| SETTING 4 | — | — | INCREASE | — |
| SETTING 5 | — | — | — | INCREASE |
| SETTING 6 | — | — | INCREASE | INCREASE |
| SETTING 7 | DECREASE | — | INCREASE | — |
| SETTING 8 | DECREASE | — | — | INCREASE |
| SETTING 9 | DECREASE | — | INCREASE | INCREASE |
| SETTING 10 | — | DECREASE | INCREASE | — |
| SETTING 11 | — | DECREASE | — | INCREASE |
| SETTING 12 | — | DECREASE | INCREASE | INCREASE |
| SETTING 13 | DECREASE | DECREASE | INCREASE | — |
| SETTING 14 | DECREASE | DECREASE | — | INCREASE |
| SETTING 15 | DECREASE | DECREASE | INCREASE | INCREASE |

FIG.10

|  | ROTATION ANGLE | NUMBER OF ROTATIONS (ROTATION ANGLE SPEED) |
| --- | --- | --- |
| SETTING A | NORMAL ROTATION < REVERSE ROTATION | — |
| SETTING B | — | NORMAL ROTATION < REVERSE ROTATION |
| SETTING C | NORMAL ROTATION < REVERSE ROTATION | NORMAL ROTATION < REVERSE ROTATION |

DENTAL TREATING APPARATUS

BACKGROUND OF THE INVENTION

1. Field of the Invention

The present invention relates to a dental treating apparatus with a hand piece, more specifically, to a dental treating apparatus that causes a cutting tool for cutting and enlarging an inner wall of a root canal of a tooth to be driven.

2. Description of the Background Art

As for a dental treating apparatus with a hand piece, there is, for example, an apparatus for providing treatment by attaching a cutting tool to a head unit of a hand piece and driving the cutting tool to cut and enlarge a root canal of a tooth. U.S. Pat. No. 3,264,607 (PTL 1), U.S. Pat. No. 3,676,753 (PTL 2) and U.S. Pat. No. 3,615,209 (PTL 3) disclose various types of driving control in order to, for example, prevent breakage due to a load applied to the cutting tool when the dental treating apparatus causes the cutting tool to be driven to cut and enlarge the root canal of the tooth.

A dental treating apparatus disclosed in PTL 1 includes detecting means for detecting a load applied to a cutting tool, and control means for reversely rotating a cutting tool driving motor when the detected load reaches a preset reference.

A dental treating apparatus disclosed in PTL 2 includes driving means for driving a cutting tool, load detecting means for detecting a load applied to the cutting tool, root canal length measuring means for measuring a root canal length by using the cutting tool, reference load setting means for arbitrarily presetting a reference load, and control means for controlling the driving means. When the load detected by the load detecting means exceeds the reference load, the control means controls the driving means by any one of the operations of stopping driving of the cutting tool, reducing an amount of driving, reversing rotation, and repeating normal rotation and reverse rotation, such that the load applied to the cutting tool is reduced. Furthermore, based on a value of the root canal length measured by the root canal length measuring means, the control means controls the driving means such that the amount of driving the cutting tool becomes smaller as a distance from the cutting tool to a root apex becomes shorter.

A dental treating apparatus disclosed in PTL 3 includes driving means for driving a cutting tool, root canal length measuring means for measuring a root canal length, and control means for controlling the driving means such that the driving force of the cutting tool changes in accordance with a value of the root canal length measured by the root canal length measuring means. The control means includes number-of-rotations control means for controlling the number of rotations of the cutting tool. Based on the value of the root canal length measured by the root canal length measuring means, the number-of-rotations control means controls the driving means such that the number of rotations of the cutting tool becomes smaller as a distance from the cutting tool to a root apex becomes shorter.

In addition to a cutting tool having a blade formed such that the cutting tool is rotated in one direction to cut a tooth, there has recently been a cutting tool having a blade formed such that the cutting tool is rotated alternately in one direction and in the opposite direction to cut a tooth. Japanese National Patent Publication. No. 2003-504113 (PTL 4) discloses a dental treating apparatus that causes the cutting tool to be driven to rotate alternately in one direction and in the opposite direction.

In the dental treating apparatus disclosed in PTL 4, the cutting tool is rotated clockwise or counterclockwise by a desired first rotation angle, and subsequently, is rotated in a direction opposite to the first rotation angle by a second rotation angle. The first rotation angle is larger than the second rotation angle such that a cut piece is discharged from a surface of a root canal to the above.

The root canal of the tooth, which is an object to be cut, is thin and curved. Therefore, the cutting tool of the dental treating apparatus must be inserted into the curved root canal to cut and enlarge the root canal. A highly-flexible nickel titanium alloy and the like are used as a material of the cutting tool to cut and enlarge the curved root canal. However, application of excessive load results in breakage of the cutting tool. Therefore, the cutting tool of the dental treating apparatus must be driven such that the excessive load is not applied to the cutting tool.

If the excessive load is applied and the cutting tool is broken when the cutting tool is cutting and enlarging the root canal of the tooth, the tooth must be cut more than necessary in order to remove the cutting tool from the root canal. Furthermore, if the cutting tool cannot be removed from the root canal, the tooth itself must be drawn.

As for the dental treating apparatus that causes the cutting tool to be driven with normal driving in which the cutting tool is rotated in one direction, PTLs 1 to 3 suggest control for driving the cutting tool such that the excessive load is not applied. However, as for the dental treating apparatus that causes the cutting tool to be driven with twist driving in which the cutting tool is rotated alternately in one direction and in the opposite direction, PTL 4 and the like do not suggest control for driving the cutting tool such that the excessive load is not applied.

SUMMARY OF THE INVENTION

The present invention provides a dental treating apparatus in which breakage of a cutting tool and excessive cutting can be prevented and safe cutting can be achieved even when the cutting tool is driven with twist driving.

A dental treating apparatus according to the present invention includes: a hand piece; a power source; a driving unit; a driving state detecting unit; and a controller. The hand piece drivably holds a cutting tool on a head unit. The power source drives the cutting tool. When a rotation direction in which the cutting tool cuts an object to be cut is defined as normal rotation and a rotation direction opposite to the normal rotation is defined as reverse rotation, the driving unit drives the cutting tool with twist driving in which the normal rotation and the reverse rotation are repeated. The driving state detecting unit detects a driving state of the cutting tool. The controller changes at least one parameter of a rotation angle in the normal rotation, a rotation angle speed in the normal rotation, a rotation angle in the reverse rotation, and a rotation angle speed in the reverse rotation in accordance with the driving state of the cutting tool detected by the driving state detecting unit.

In the dental treating apparatus according to the present invention, at least one parameter of the rotation angle in the normal rotation, the rotation angle speed in the normal rotation, the rotation angle in the reverse rotation, and the rotation angle speed in the reverse rotation is changed in accordance with the driving state of the cutting tool. Therefore, the stress applied to the cutting tool for cutting and enlarging the root canal can be limited to within an appropriate range, and breakage of the cutting tool and excessive cutting can be prevented and safe cutting can be achieved.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 9 is a diagram showing combinations of parameters that are changed in accordance with a load applied to the cutting tool.

FIG. 10 is a diagram showing a relationship among the parameters that are changed in accordance with the load applied to the cutting tool.

DESCRIPTION OF THE PREFERRED EMBODIMENTS

Hereinafter, embodiments of the present invention are described with reference to the drawings.

First Embodiment

A dental treating apparatus according to a first embodiment of the present invention is a root canal treating device including a root canal enlarging and root canal length measuring system into which a dental hand piece for treatment on a root canal is incorporated. The dental treating apparatus according to the present invention is, however, not limited to the root canal treating device, and can be applied to a dental treating apparatus with a similar configuration.

Figure 1:
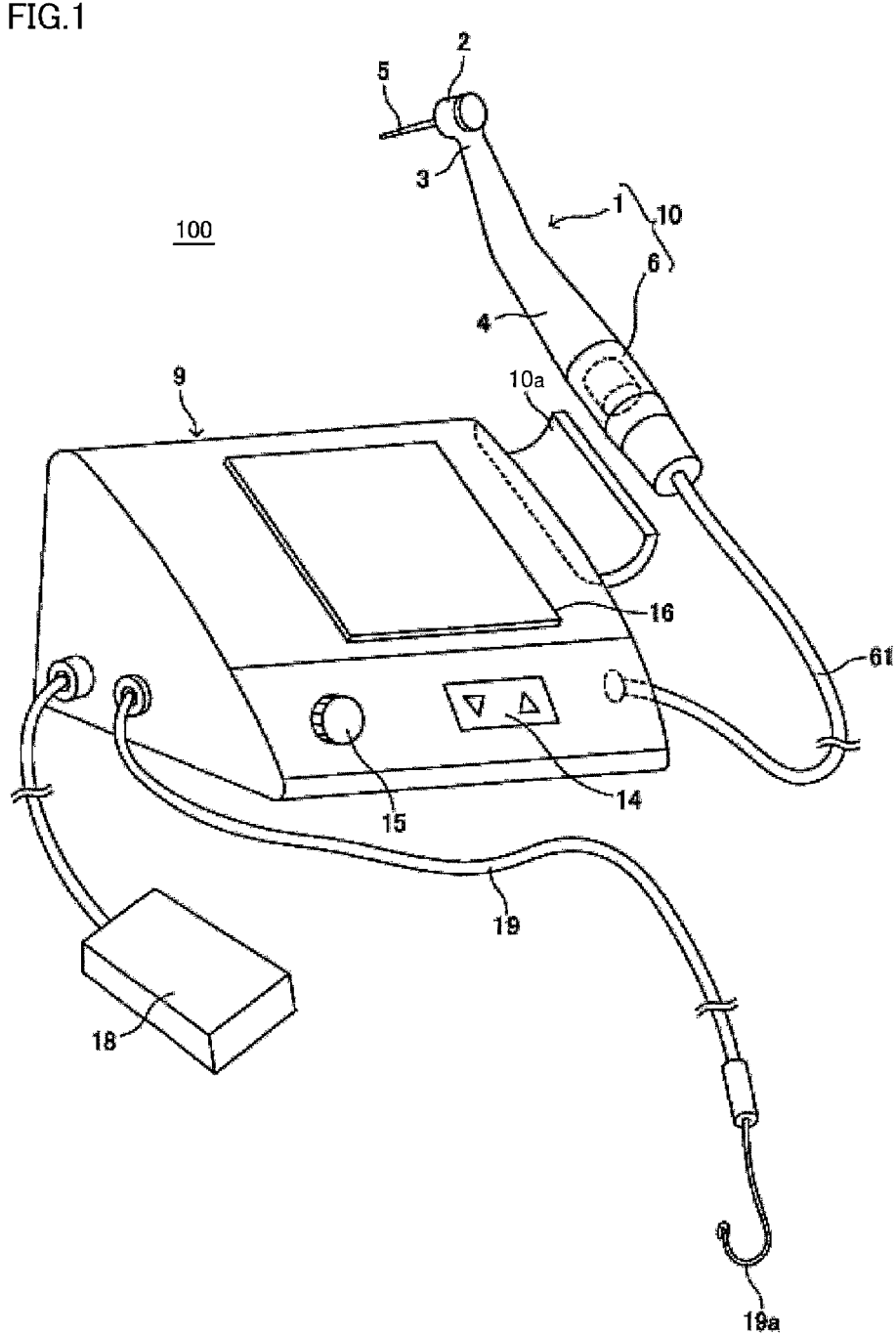
FIG. 1 is a schematic diagram showing an appearance of a configuration of a root canal treating device according to a first embodiment of the present invention.
Figure 2:
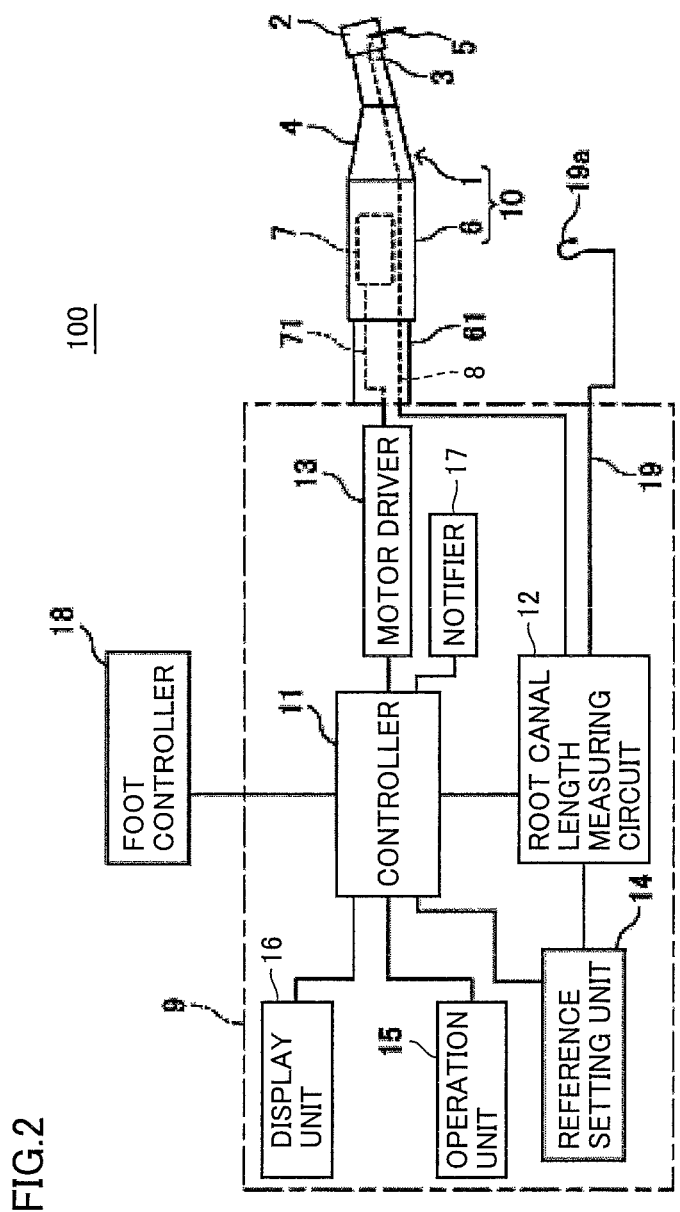
FIG. 2 is a block diagram showing a configuration of functions of the root canal treating device according to the first embodiment of the present invention.

FIG. 1 is a schematic diagram showing an appearance of a configuration of the root canal treating device according to the first embodiment of the present invention. FIG. 2 is a block diagram showing a configuration of functions of the root canal treating device according to the first embodiment of the present invention. A root canal treating device 100 as shown in FIG. 1 includes a hand piece 1, a motor unit 6 and a control box 9 for treating dental root canal.

Hand piece 1 for treating the dental root canal includes a head unit 2, a neck unit 3 with a small diameter connected to head unit 2, and a grip 4 connected to neck unit 3 and gripped by a hand or fingers. Further, to a base unit of grip 4, motor unit 6 is detachably connected for rotating and driving a cutting tool 5 to be held on head unit 2. A dental instrument 10 is configured with hand piece 1 and motor unit 6 coupled to each other.

As shown in FIG. 2, a micro motor 7 is embedded in motor unit 6 that is connected to control box 9 through a hose 61 containing therein a power supply lead 71 for supplying power to micro motor 7, a signal lead 8 for transmitting a signal to a root canal length measuring circuit 12 to be described below, and the like. Here, signal lead 8 is a part of a conductive body for transmitting an electric signal, signal lead 8 being electrically connected to cutting tool 5 through motor unit 6 and hand piece 1. It is also noted that cutting tool 5 is one of electrodes of root canal length measuring circuit 12.

Control box 9 includes a controller 11, root canal length measuring circuit 12, a motor driver 13, a reference setting unit 14, an operation unit 15, a display unit 16, a notifier 17, and the like. As shown in FIG. 1, it should be noted that control box 9 is provided with a holder 10a holding instrument 10 when instrument 10 is not used, at a lateral part of a body. Also, in control box 9, foot controller 18 is connected to controller 11 and lead 19 is connected to root canal length measuring circuit 12. Lead 19 may be in a form that is bifurcated at an intermediate portion of hose 61. A mouth electrode 19a hung on a lip of a patient is attached to a tip end of lead 19 in an electrically conductive state. It should be noted that mouth electrode 19a is the other one of the electrodes of root canal length measuring circuit 12.

A primary part of controller 11 for controlling the whole system for enlarging the root canal and measuring the root canal length is configured by a microcomputer. Root canal length measuring circuit 12, motor driver 13, reference setting unit 14, operation unit 15, display unit 16, notifier 17, and foot controller 18 are connected to controller 11. When a rotation direction in which cutting tool 5 cuts an object to be cut is defined as normal rotation and a rotation direction opposite to the normal rotation is defined as reverse rotation, controller 11 can execute twist driving in which cutting tool 5 is driven such that the normal rotation and the reverse rotation are repeated. Controller 11 can change parameters of a rotation angle in the normal rotation, a rotation angle speed (the number of rotations) in the normal rotation, a rotation angle in the reverse rotation, and a rotation angle speed in the reverse rotation, and can drive cutting tool 5. It should be noted that controller 11 can also execute normal rotation driving in which the rotation angle or the rotation angle speed in the reverse rotation is set to be "0" and cutting tool 5 is normally rotated and driven as well as reverse rotation driving in which the rotation angle or the rotation angle speed in the normal rotation is set to be "0" and cutting tool 5 is reversely rotated and driven.

Here, the rotation angle speed refers to an amount representing a speed of rotation of cutting tool 5, and the number of rotations per unit time is obtained by dividing the rotation angle speed by $2\pi$ radian. In the embodiments below, the speed of rotation of cutting tool 5 is expressed by using the number of rotations, instead of using the rotation angle speed. It should be noted that the number of rotations is expressed in the unit of revolutions per minute (rpm).

Root canal length measuring circuit 12 configures a closed circuit with cutting tool 5 inserted in the root canal of the tooth as one electrode and mouth electrode 19a hung on the lip of the patient as the other electrode. Root canal length measuring circuit 12 can measure a distance from an apical position of the tooth to a tip end of cutting tool 5 by applying voltage between cutting tool 5 and mouth electrode 19a and measuring impedance between cutting tool 5 and mouth electrode 19a. An amount of insertion of cutting tool 5, that is, a distance from an opening of the root canal to the tip end of cutting tool 5, when root canal length measuring circuit 12 detects that the tip end of cutting tool 5 has reached the apical position can be defined as the root canal length. It should be noted that a method for electrically measuring the root canal length by measuring the impedance between cutting tool 5 and mouth electrode 19a is publicly known and all publicly-known methods for electrically measuring the root canal length can be applied to root canal treating device 100 according to the first embodiment of the present invention.

Motor driver 13 is connected to micro motor 7 via power supply lead 71 and controls the power supplied to micro motor 7 based on a control signal from controller 11. Motor driver 13 can control the rotation direction, the number of rotations, the rotation angle and the like of micro motor 7, namely the rotation direction, the number of rotations, the rotation angle and the like of cutting tool 5 by controlling the power supplied to micro motor 7.

Reference setting unit 14 sets a reference for controlling the rotation direction, the number of rotations, the rotation angle and the like of cutting tool 5. For example, reference setting unit 14 presets the apical position and a position located at a prescribed distance from the apical position as reference positions by using root canal length measuring circuit 12, and changes parameters of the rotation direction, the number of rotations and the rotation angle of cutting tool 5 when the tip end of cutting tool 5 reaches these reference positions. In addition, reference setting unit 14 presets a load allowed by cutting tool 5 as a reference load, and changes the parameters of the rotation direction, the number of rotations and the rotation angle of cutting tool 5 when a load applied to cutting tool 5 becomes equal to or larger than this reference load.

Operation unit 15 can set the parameters of the number of rotations and the rotation angle of cutting tool 5, and can also select whether or not the root canal length is measured. Operation unit 15 can also manually switch between the normal rotation driving and the reverse rotation driving, and can also manually switch between the normal rotation driving and the twist driving.

Display unit 16 displays a position of the tip end of cutting tool 5 in the root canal as well as the rotation direction, the number of rotations, the rotation angle and the like of cutting tool 5 as described below. Also, display unit 16 can display information for notifier 17 to notify a user.

Notifier 17 notifies the user by light, sound, vibration, and the like of the driving state of cutting tool 5 that is being executed by controller 11. Specifically, notifier 17 includes an LED (Light Emitting Diode), a speaker, an oscillator, and the like according to the need to notify the user of the driving state of cutting tool 5, and colors of the light emitted from the LED change or sounds outputted from the speaker change based on whether the normal driving is being executed or the twist driving is being executed. Also, notifier 17 need not include the LED, the speaker, the oscillator and the like separately if display unit 16 can display the driving state of cutting tool 5 for the user.

Foot controller 18 is an operation unit for performing driving control on cutting tool 5 by micro motor 7 by a stepping operation. It should be noted that the driving control on cutting tool 5 by micro motor 7 is not limited to foot controller 18, namely, an operation switch (not shown) is provided in grip 4 of hand piece 1 to perform the driving control on cutting tool 5 by this operation switch and foot controller 18. Also for example, in a state where the stepping operation via foot controller 18 is performed, the rotation of cutting tool 5 may be started by detecting, using root canal length measuring circuit 12, that cutting tool 5 is inserted into the root canal.

It should be noted that a configuration is disclosed in that control box 9 of root canal treating device 100 is put on, a tray table or a side table installed on a lateral part of a dental treatment table and used. The present invention is, however, not limited to such a configuration but can include a configuration in that control box 9 is incorporated into the tray table or the side table.

Figure 3:
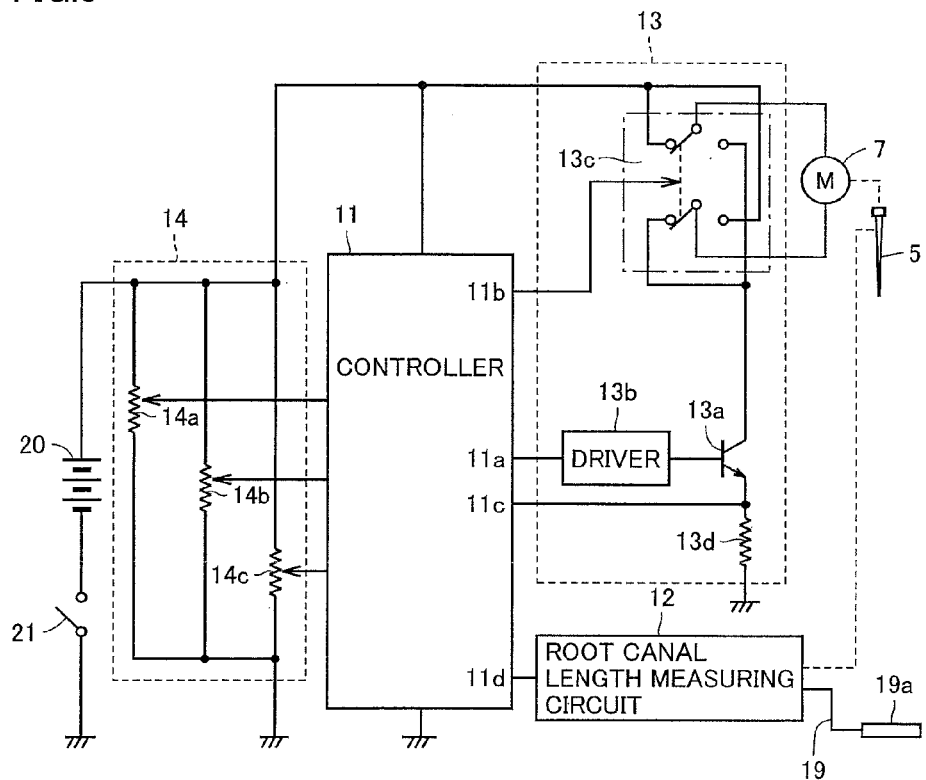
FIG. 3 is a circuit diagram showing a circuit configuration of the root canal treating device according to the first embodiment of the present invention.

Next, a circuit configuration of root canal treating device 100 for performing the driving control on cutting tool 5 is described in more details. FIG. 3 is a circuit diagram showing a circuit configuration of root canal treating device 100 according to the first embodiment of the present invention. In root canal treating device 100 shown in FIG. 3, components of micro motor 7, controller 11, root canal length measuring circuit 12, motor driver 13, and reference setting unit 14 that are involved in the driving control on cutting tool 5 are illustrated.

Furthermore, motor driver 13 includes a transistor switch 13a, a transistor driver circuit 13b, a rotation direction switching switch 13c, and a resistor 13d for load detection. Reference setting unit 14 includes a variable resistor 14a for setting the reference load, a variable resistor 14b for setting a duty, and a variable resistor 14c for setting the reference position. Reference setting unit 14 is connected to a main power supply 20 for root canal treating device 100, and a main switch 21. Cutting tool 5 is held on micro motor 7 via an appropriate gear mechanism and the like, although not shown.

Transistor driver circuit 13b operates in response to a control signal outputted from a port 11a of controller 11, and controls ON/OFF of transistor switch 13a and drives micro motor 7. Micro motor 7 rotates normally or reversely in accordance with a state of rotation direction switching switch 13c. When the control signal outputted from port 11a of controller 11 has, for example, a pulse waveform repeated in a certain cycle, a width of the pulse waveform, that is a duty ratio is adjusted by variable resistor 14b for setting a duty in reference setting unit 14. Micro motor 7 drives cutting tool 5 at the number of rotations corresponding to this duty ratio.

In response to a control signal outputted from a port 11b of controller 11, rotation direction switching switch 13c switches between rotating normally and driving cutting tool 5 and rotating reversely and driving cutting tool 5. Controller 11 receives a resistance value of resistor 13d for load detection at a port 11c and detects a load applied to cutting tool 5. Furthermore, controller 11 receives the root canal length measured by root canal length measuring circuit 12 at a port 11d. Resistor 13d for load detection and root canal length measuring circuit 12 function as a driving state detecting unit for detecting the driving state of cutting tool 5. With the configuration described above, micro motor 7 and cutting tool 5 are driven in various driving methods such as the normal rotation driving, the reverse rotation driving, and the twist driving in which the normal rotation and the reverse rotation by prescribed angles are repeated.

Figure 4:
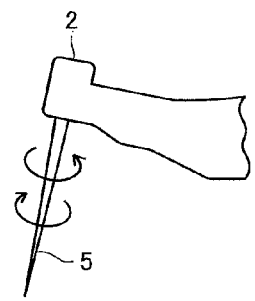
FIG. 4 is a schematic diagram showing a rotation direction of a cutting tool in the case of twist driving.

FIG. 4 is a schematic diagram showing a rotation direction of cutting tool 5 in the case of the twist driving. In the twist driving shown in FIG. 4, the normal rotation in which cutting tool 5 is rotated clockwise as directed toward the tip end of cutting tool 5 and the reverse rotation in which cutting tool 5 is rotated counterclockwise are executed alternately. For example, in the twist driving, rotation in the normal rotation direction by a rotation angle of 90° and rotation in the reverse rotation direction by a rotation angle of 30° are executed alternately.

Figure 5:
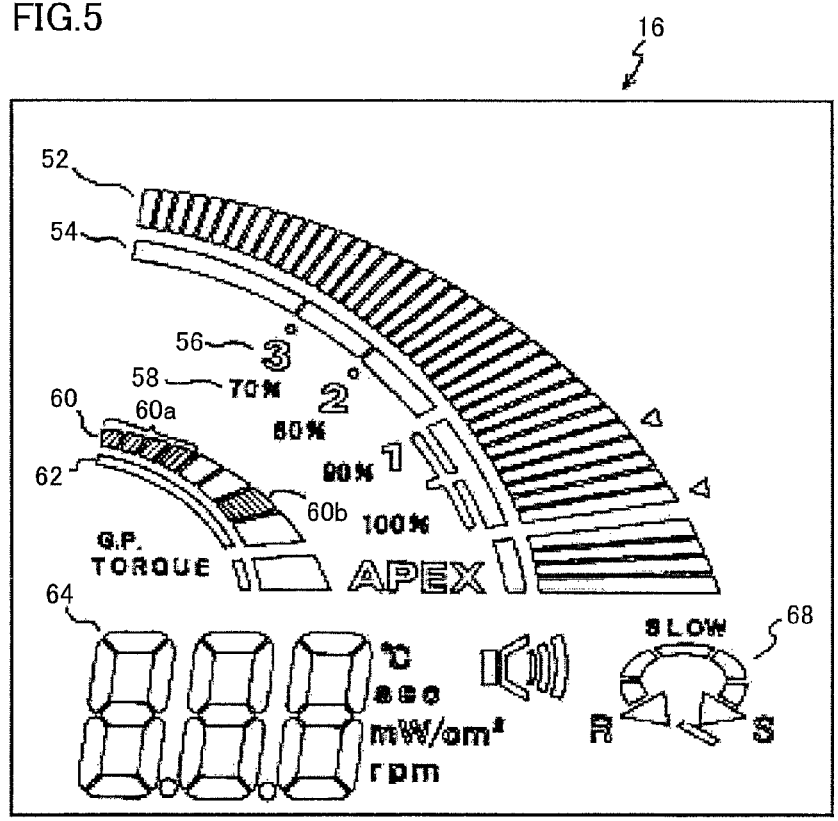
FIG. 5 is a diagram showing a display example of a liquid crystal display panel of a display unit shown in FIG. 1.

Next, display of a liquid crystal display panel of display unit 16 shown in FIG. 1 is described. FIG. 5 is a diagram showing a display example of the liquid crystal display panel of display unit 16 shown in FIG. 1.

Display unit 16 shown in FIG. 5 is the liquid crystal display panel, and is provided with a dot display unit 52 including many elements for displaying the measured root canal, length in detail, a zone display unit 54 for zoning and displaying the root canal length in a stepwise manner, a boundary display unit 56 for displaying a boundary of each zone, and an arrival rate display unit 58 for displaying a rate of arrival at the root apex.

Dot display unit 52 is configured such that the elements are sequentially displayed from the top to the bottom as the tip end of cutting tool 5 comes closer to the root apex. A position of the gauge "APEX" shows a position of the root apex, and arrival of the elements at this gauge means that the tip end of cutting tool 5 has nearly arrived at the position of the root apex.

Display unit 16 is also provided with a dot display unit 60 including many elements for displaying the load detected by resistor 13d for load detection, and a zone display unit 62 for zoning and displaying the load in a stepwise manner. Dot display unit 60 is configured such that the elements are sequentially displayed from the top to the bottom as the load detected by resistor 13d for load detection becomes larger.

For example, the load applied to cutting tool 5 when cutting tool 5 is cutting the tooth is displayed on dot display unit 60 by diagonally shaded elements 60a. In order to prevent frequent switching of displays, dot display unit 60 may have a peak hold function to display, for a certain time period, a maximum value of the load detected within a prescribed time period.

An element 60b corresponding to the reference load set by variable resistor 14a for setting the reference load may be displayed on dot display unit 60. By displaying element 60b on dot display unit 60, it can be visualized how much margin the load detected by resistor 13d for load detection has with respect to the reference load.

Display unit 16 is further provided with a numerical value display unit 64 for numerically displaying the number of rotations of cutting tool 5 and the load applied to cutting tool 5, and a rotation display unit 68 for displaying the orientation of rotation of cutting tool 5 (normal rotation S, reverse rotation R) and the magnitude of the number of rotations of cutting tool 5.

Next, description is given to driving of cutting tool 5 of root canal treating device 100 according to the first embodiment. In root canal treating device 100 according to the first embodiment, cutting tool 5 is driven with the normal rotation driving, not the twist driving, at the start of driving, and cutting tool 5 is driven with the twist driving when the load applied to cutting tool 5 becomes equal to or larger than a reference load A (second reference load). After cutting tool 5 is driven with the twist driving, controller 11 of root canal treating device 100 changes at least one parameter of the rotation angle in the normal rotation and the rotation angle speed in the normal rotation such that the parameter becomes smaller as the load becomes larger, or changes at least one parameter of the rotation angle in the reverse rotation and the rotation angle speed in the reverse rotation such that the parameter becomes larger as the load becomes larger, in order that the load applied to cutting tool 5 becomes equal to or smaller than a reference load B. When the load applied to cutting tool 5 becomes equal to or larger than a reference load C (first reference load), controller 11 of root canal treating device 100 drives cutting tool 5 with the reverse rotation driving or stops driving. A value of the load becomes larger in the order of reference load A, reference load B and reference load C.

Figure 6:
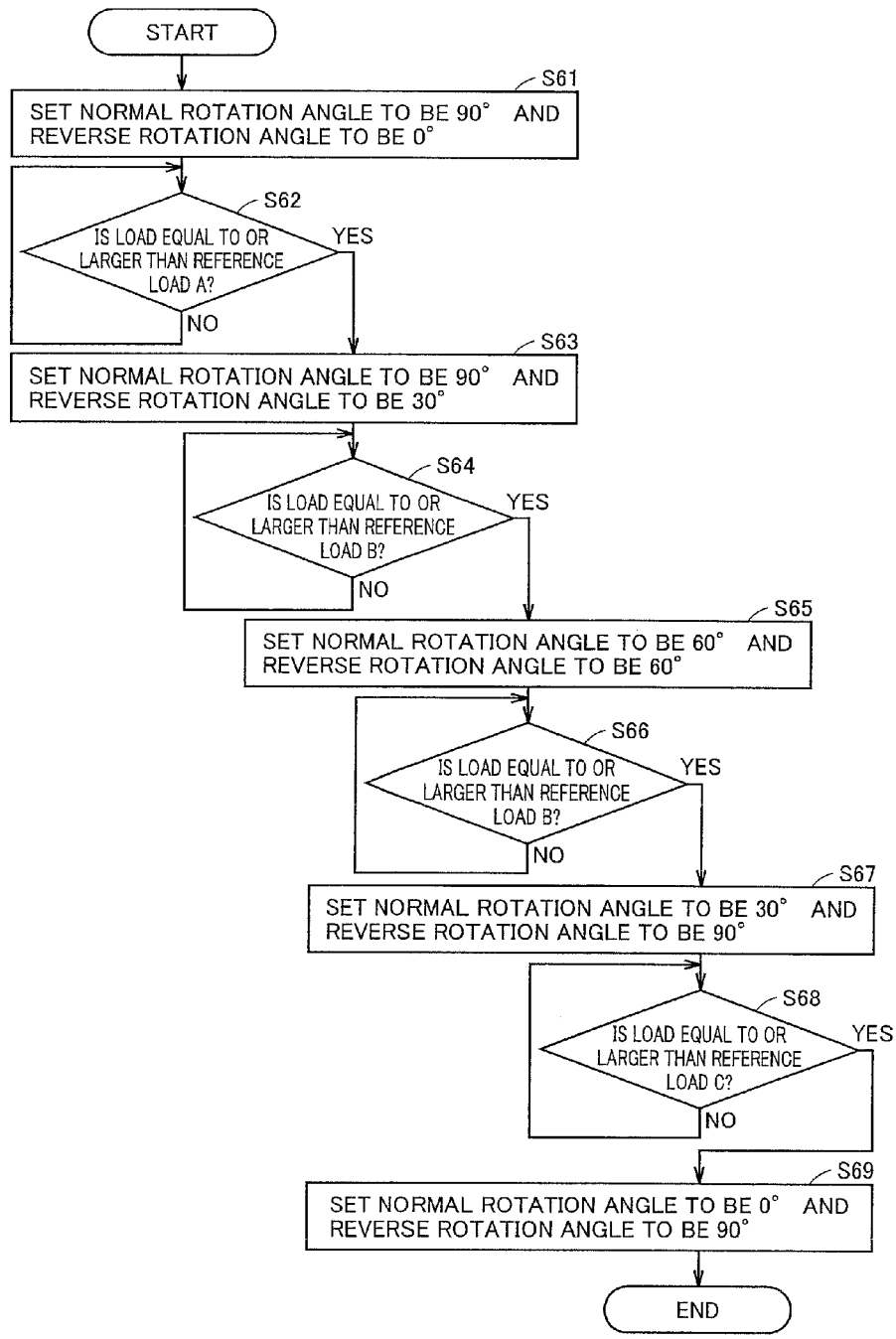
FIG. 6 is a flowchart for describing an example of driving of the cutting tool of the root canal treating device according to the first embodiment of the present invention.

FIG. 6 is a flowchart for describing an example of driving of cutting tool 5 of root canal treating device 100 according to the first embodiment of the present invention. First, controller 11 sets the rotation angle in the nominal rotation direction (hereinafter also simply referred to as normal rotation angle) to be 90° and the rotation angle in the reverse rotation direction (hereinafter also simply referred to as reverse rotation angle) to be 0°, and drives cutting tool 5 (step S61). Since the reverse rotation angle is set to be 0°, controller 11 of root canal treating device 100 rotates cutting tool 5 in the normal rotation direction continuously and executes the normal rotation driving. Initial values set by controller 11 are used as the number of rotations in the normal rotation direction (hereinafter also simply referred to as the number of normal rotations) and the number of rotations in the reverse rotation direction (hereinafter also simply referred to as the number of reverse rotations), and the values are not changed in the process in the flowchart shown in FIG. 6.

Next, controller 11 determines whether or not the load detected by resistor 13d for load detection is equal to or larger than reference load A (step S62). Reference load A is a reference value at which driving of cutting tool 5 changes from the normal rotation driving to the twist driving, and is preset using variable resistor 14a for setting the reference load in reference setting unit 14. Therefore, when the load detected by resistor 13d for load detection is less than reference load A, controller 11 of root canal treating device 100 drives cutting tool 5 only with the normal rotation driving.

If controller 11 determines that the load detected by resistor 13d for load detection is equal to or larger than reference load A (YES in step S62), controller 11 sets the normal rotation angle to be 90° and the reverse rotation angle to be 30°, and drives cutting tool 5 (step S63). In other words, controller 11 of root canal treating device 100 increases the reverse rotation angle from 0° to 30° and drives cutting tool 5 with the twist driving such that the load applied to cutting tool 5 becomes smaller. If controller 11 determines that the load detected by resistor 13d for load detection is less than reference load A (NO in step S62), controller 11 keeps the parameters set in step S61 and continues driving of cutting tool 5.

Next, controller 11 determines whether or not the load detected by resistor 13d for load detection is equal to or larger than reference load B (step S64). Reference load B is an upper limit value of the load that can be applied to cutting tool 5 to prevent excessive cutting and safely cut and enlarge the root canal, and is preset using variable resistor 14a for setting the reference load in reference setting unit 14. In addition, reference load B is displayed by element 60b on display unit 16 shown in FIG. 5.

If controller 11 determines that the load detected by resistor 13d for load detection is equal to or larger than reference load B (YES in step S64), controller 11 sets the normal rotation angle to be 60° and the reverse rotation angle to be 60°, and drives cutting tool 5 (step S65). In other words, controller 11 of root canal treating device 100 decreases the normal rotation angle from 90° to 60°, increases the reverse rotation angle from 30° to 60° and drives cutting tool 5 with the twist driving such that the load applied to cutting tool 5 becomes smaller than reference load. B. If controller 11 determines that the load detected by resistor 13d for load detection is less than reference load B (NO in step S64), controller 11 keeps the parameters set in step S63 and continues driving of cutting tool 5.

Next, controller 11 determines whether or not the load detected by resistor 13d for load detection is equal to or larger than reference load B (step S66). Controller 11 must determine whether or not the load applied to cutting tool 5 is equal to or larger than reference load B, because an additional load may be applied to cutting tool 5 in some cases after cutting tool 5 is driven with the parameters changed in step S65 being kept.

If controller 11 determines that the load detected by resistor 13d for load detection is equal to or larger than reference load B (YES in step S66), controller 11 sets the normal rotation angle to be 30° and the reverse rotation angle to be 90°, and drives cutting tool 5 (step S67). In other words, controller 11 of root canal treating device 100 decreases the normal rotation angle from 60° to 30°, increases the reverse rotation angle from 60° to 90° and drives cutting tool 5 with the twist driving such that the load applied to cutting tool 5 becomes smaller than reference load B. If controller 11 determines that the load detected by resistor 13d for load detection is less than reference load B (NO in step S66), controller 11 keeps the parameters set in step S65 and continues driving of cutting tool 5.

Next, controller 11 determines whether or not the load detected by resistor 13d for load detection is equal to or larger than reference load C (step S68). Reference load C is a limit value of the load at which there is a high possibility of breakage of cutting tool 5, and is preset using variable resistor 14a for setting the reference load in reference setting unit 14. When the load applied to cutting tool 5 is equal to or larger than reference load C even if the parameters are changed and cutting tool 5 is driven, controller 11 executes driving for avoiding the breakage of cutting tool 5.

If controller 11 determines that the load detected by resistor 13d for load detection is equal to or larger than reference load C (YES in step S68), controller 11 sets the normal rotation angle to be 0° and the reverse rotation angle to be 90°, and drives cutting tool 5 (step S69). Since the normal rotation angle is set to be 0°, controller 11 of root canal treating device 100 rotates cutting tool 5 in the reverse rotation direction continuously and executes the reverse rotation driving. In other words, controller 11 of root canal treating device 100 drives cutting tool 5 with the reverse rotation driving in order to avoid the breakage of cutting tool 5. It should be noted that controller 11 of root canal treating device 100 may stop driving of cutting tool 5 in order to avoid the breakage of cutting tool 5. If controller 11 determines that the load detected by resistor 13d for load detection is less than reference load C (NO in step S68), controller 11 keeps the parameters set in step S67 and continues driving of cutting tool 5.

Description has been given to the example in which controller 11 of root canal treating device 100 changes the parameter of the rotation angle in a stepwise manner and drives cutting tool 5 in steps S61 to S69. The present invention is not, however, limited thereto. Controller 11 may change the parameter of the rotation angle continuously in accordance with the load applied to cutting tool 5. For example, controller 11 changes the parameter of the normal rotation angle or the reverse rotation angle from 90° to 0° continuously in accordance with a change in the load applied to cutting tool 5 from reference load A to reference load C. In addition, the upper limit values of the normal rotation angle and the reverse rotation angle are not limited to 90°. The rotation angle may be 90° or larger and the load may be set in accordance therewith.

Description has been given to the example in which controller 11 changes the parameter of the rotation angle in accordance with the load applied to cutting tool 5 in the flowchart shown in FIG. 6. Controller 11 may, however, change the parameter of the number of rotations in accordance with the load applied to cutting tool 5.

Figure 7:
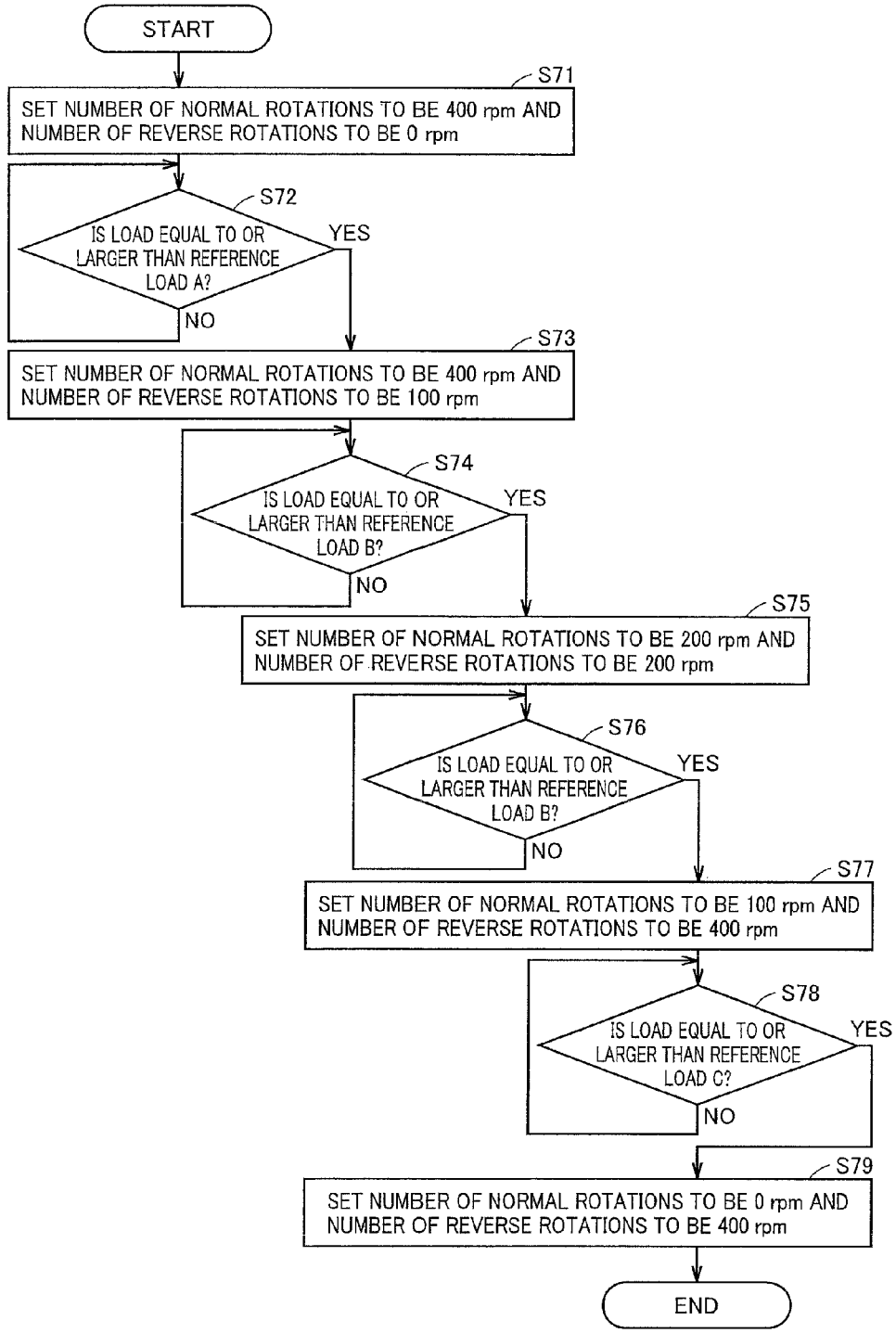
FIG. 7 is a flowchart for describing another example of driving of the cutting tool of the root canal treating device according to the first embodiment of the present invention.

FIG. 7 is a flowchart for describing another example of driving of cutting tool 5 of root canal treating device 100 according to the first embodiment of the present invention. First, controller 11 sets the number of normal rotations to be 400 rpm and the number of reverse rotations to be 0 rpm, and drives cutting tool 5 (step S71). Since the number of reverse rotations is set to be 0 rpm, controller 11 of root canal treating device 100 rotates cutting tool 5 in the normal rotation direction continuously and executes the normal rotation driving. Initial values set by controller 11 are used as the normal rotation angle and the reverse rotation angle, and the values are not changed in the process in the flowchart shown in FIG. 7.

Next, controller 11 determines whether or not the load detected by resistor 13d for load detection is equal to or larger than reference load A (step S72). When the load detected by resistor 13d for load detection is less than reference load A, controller 11 of root canal treating device 100 drives cutting tool 5 only with the normal rotation driving.

If controller 11 determines that the load detected by resistor 13d for load detection is equal to or larger than reference load A (YES in step S72), controller 11 sets the number of normal rotations to be 400 rpm and the number of reverse rotations to be 100 rpm, and drives cutting tool 5 (step S73). In other words, controller 11 of root canal treating device 100 increases the number of reverse rotations from 0 rpm to 100 rpm and drives cutting tool 5 with the twist driving such that the load applied to cutting tool 5 becomes smaller. If controller 11 determines that the load detected by resistor 13d for load detection is less than reference load A (NO in step S72), controller 11 keeps the parameters set in step S71 and continues driving of cutting tool 5.

Next, controller 11 determines whether or not the load detected by resistor 13d for load detection is equal to or larger than reference load B (step S74).

If controller 11 determines that the load detected by resistor 13d for load detection is equal to or larger than reference load B (YES in step S74), controller 11 sets the number of normal rotations to be 200 rpm and the number of reverse rotations to be 200 rpm, and drives cutting tool 5 (step S75). In other words, controller 11 of root canal treating device 100 decreases the number of normal rotations from 400 rpm to 200 rpm, increases the number of reverse rotations from 100 rpm to 200 rpm and drives cutting tool 5 with the twist driving such that the load applied to cutting tool 5 becomes smaller than reference load B. If controller 11 determines that the load detected by resistor 13*d* for load detection is less than reference load B (NO in step S74), controller 11 keeps the parameters set in step S73 and continues driving of cutting tool 5.

Next, controller 11 determines whether or not the load detected by resistor 13*d* for load detection is equal to or larger than reference load B (step S76). Controller 11 must determine whether or not the load applied to cutting tool 5 is equal to or larger than reference load B, because an additional load may be applied to cutting tool 5 in some cases after cutting tool 5 is driven with the parameters changed in step S75 being kept.

If controller 11 determines that the load detected by resistor 13*d* for load detection is equal to or larger than reference load B (YES in step S76), controller 11 sets the number of normal rotations to be 100 rpm and the number of reverse rotations to be 400 rpm, and drives cutting tool 5 (step. S77). In other words, controller 11 of root canal treating device 100 decreases the number of normal rotations from 200 rpm to 100 rpm, increases the number of reverse rotations from 200 rpm to 400 rpm and drives cutting tool 5 with the twist driving such that the load applied to cutting tool 5 becomes smaller than reference load B. If controller 11 determines that the load detected by resistor 13*d* for load detection is less than reference load B (NO in step S76), controller 11 keeps the parameters set in step S75 and continues driving of cutting tool 5.

Next, controller 11 determines whether or not the load detected by resistor 13*d* for load detection is equal to or larger than reference load C (step S78). When the load applied to cutting tool 5 is equal to or larger than reference load C even if the parameters are changed and cutting tool 5 is driven, controller 11 executes driving for avoiding the breakage of cutting tool 5.

If controller 11 determines that the load detected by resistor 13*d* for load detection is equal to or larger than reference load C (YES in step S78), controller 11 sets the number of normal rotations to be 0 rpm and the number of reverse rotations to be 400 rpm, and drives cutting tool 5 (step S79). Since the number of normal rotations is set to be 0 rpm, controller 11 of root canal treating device 100 rotates cutting tool 5 in the reverse rotation direction continuously and executes the reverse rotation driving. In other words, controller 11 of root canal treating device 100 drives cutting tool 5 with the reverse rotation driving in order to avoid the breakage of cutting tool 5. It should be noted that controller 11 of root canal treating device 100 may stop driving of cutting tool 5 in order to avoid the breakage of cutting tool 5. If controller 11 determines that the load detected by resistor 13*d* for load detection is less than reference load C (NO in step S78), controller 11 keeps the parameters set in step S77 and continues driving of cutting tool 5.

Description has been given to the example in which controller 11 of root canal treating device 100 changes the parameter of the number of rotations in a stepwise manner and drives cutting tool 5 in steps S71 to S79. The present invention is not, however, limited thereto. Controller 11 may change the parameter of the number of rotations continuously in accordance with the load applied to cutting tool 5. For example, controller 11 changes the parameter of the number of normal rotations or the number of reverse rotations from 400 rpm to 0 rpm continuously in accordance with a change in the load applied to cutting tool 5 from reference load A to reference load C. In addition, the upper limit values of the number of normal rotations and the number of reverse rotations are not limited to 400 rpm. The number of rotations may be 400 rpm or larger and the load may be set in accordance therewith.

Description has been given to the example in which controller 11 changes only the parameter of the rotation angle in accordance with the load applied to cutting tool 5 in the flowchart shown in FIG. 6, and description has been given to the example in which controller 11 changes only the parameter of the number of rotations in accordance with the load applied to cutting tool 5 in the flowchart shown in FIG. 7. Controller 11 may, however, change both parameters of the rotation angle and the number of rotations in accordance with the load applied to cutting tool 5.

Figure 8:
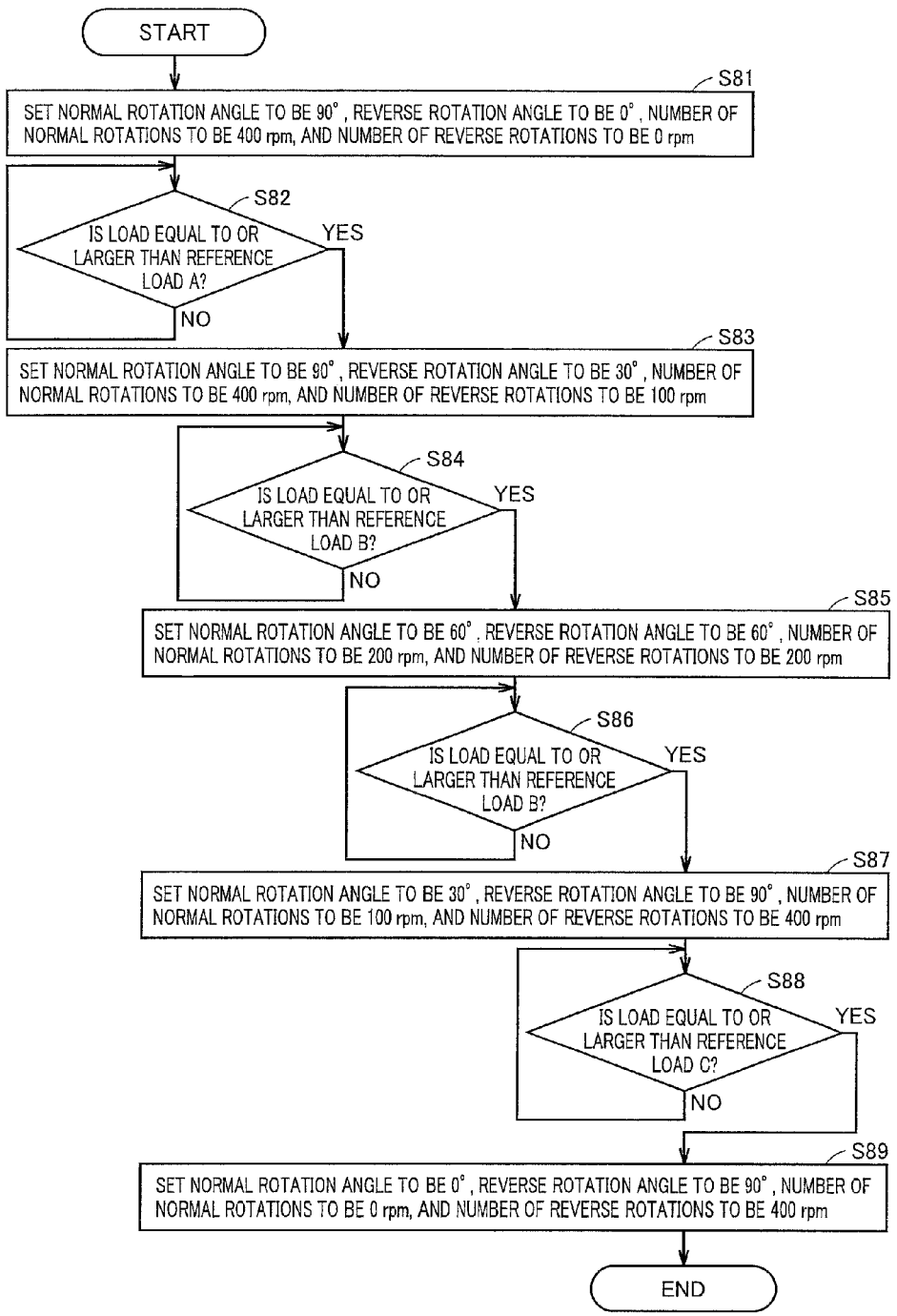
FIG. 8 is a flowchart for describing still another example of driving of the cutting tool of the root canal treating device according to the first embodiment of the present invention.

FIG. 8 is a flowchart for describing still another example of driving of cutting tool 5 of root canal treating device 100 according to the first embodiment of the present invention. First, controller 11 sets the normal rotation angle to be 90°, the reverse rotation angle to be 0', the number of normal rotations to be 400 rpm, and the number of reverse rotations to be 0 rpm, and drives cutting tool 5 (step S81). Since the reverse rotation angle is set to be 0° and the number of reverse rotations is set to be 0 rpm, controller 11 of root canal treating device 100 rotates cutting tool 5 in the normal rotation direction continuously and executes the normal rotation driving.

Next, controller 11 determines whether or not the load detected by resistor 13*d* for load detection is equal to or larger than reference load A (step S82). When the load detected by resistor 13*d* for load detection is less than reference load A, controller 11 of root canal treating device 100 drives cutting tool 5 only with the normal rotation driving.

If controller 11 determines that the load detected by resistor 13*d* for load detection is equal to or larger than reference load A (YES in step S82), controller 11 sets the normal rotation angle to be 90°, the reverse rotation angle to be 30°, the number of normal rotations to be 400 rpm, and the number of reverse rotations to be 100 rpm, and drives cutting tool 5 (step S83). In other words, controller 11 of root canal treating device 100 increases the reverse rotation angle from 0° to 30°, increases the number of reverse rotations from 0 rpm to 100 rpm and drives cutting tool 5 with the twist driving such that the load applied to cutting tool 5 becomes smaller. If controller 11 determines that the load detected by resistor 13*d* for load detection is less than reference load A (NO in step S82), controller 11 keeps the parameters set in step S81 and continues driving of cutting tool 5.

Next, controller 11 determines whether or not the load detected by resistor 13*d* for load detection is equal to or larger than reference load B (step S84).

If controller 11 determines that the load detected by resistor 13*d* for load detection is equal to or larger than reference load B (YES in step S84), controller 11 sets the normal rotation angle to be 60°, the reverse rotation angle to be 60°, the number of normal rotations to be 200 rpm, and the number of reverse rotations to be 200 rpm, and drives cutting tool 5 (step S85). In other words, controller 11 of root canal treating device 100 decreases the normal rotation angle from 90° to 60°, decreases the number of normal rotations from 400 rpm to 200 rpm, increases the reverse rotation angle from 30° to 60°, increases the number of reverse rotations from 100 rpm to 200 rpm, and drives cutting tool 5 with the twist driving such that the load applied to cutting tool 5 becomes smaller than reference load B. If controller 11 determines that the load detected by resistor 13*d* for load detection is less than reference load B (NO in step S84), controller 11 keeps the parameters set in step S83 and continues driving of cutting tool 5.

Next, controller 11 determines whether or not the load detected by resistor 13*d* for load detection is equal to or larger than reference load B (step S86). Controller 11 must determine whether or not the load applied to cutting tool 5 is equal to or larger than reference load B, because an additional load may be applied to cutting tool 5 in some cases after cutting tool 5 is driven with the parameters changed in step S85 being kept.

If controller 11 determines that the load detected by resistor 13*d* for load detection is equal to or larger than reference load B (YES in step S86), controller 11 sets the normal rotation angle to be 30°, the reverse rotation angle to be 90°, the number of normal rotations to be 100 rpm, and the number of reverse rotations to be 400 rpm, and drives cutting tool 5 (step S87). In other words, controller 11 of root canal treating device 100 decreases the normal rotation angle from 60° to 30°, decreases the number of normal rotations from 200 rpm to 100 rpm, increases the reverse rotation angle from 60° to 90°, increases the number of reverse rotations from 200 rpm to 400 rpm, and drives cutting tool 5 with the twist driving such that the load applied to cutting tool 5 becomes smaller than reference load B. If controller 11 determines that the load detected by resistor 13*d* for load detection is less than reference load B (NO in step S86), controller 11 keeps the parameters set in step S85 and continues driving of cutting tool 5.

Next, controller 11 determines whether or not the load detected by resistor 13*d* for load detection is equal to or larger than reference load C (step S88). When the load applied to cutting tool 5 is equal to or larger than reference load C even if the parameters are changed and cutting tool 5 is driven, controller 11 executes driving for avoiding the breakage of cutting tool 5.

If controller 11 determines that the load detected by resistor 13*d* for load detection is equal to or larger than reference load C (YES in step S88), controller 11 sets the normal rotation angle to be 0°, the reverse rotation angle to be 90°, the number of normal rotations to be 0 rpm, and the number of reverse rotations to be 400 rpm, and drives cutting tool 5 (step S89). Since the normal rotation angle is set to be 0° and the number of normal rotations is set to be 0 rpm, controller 11 of root canal treating device 100 rotates cutting tool 5 in the reverse rotation direction continuously and executes the reverse rotation driving. In other words, controller 11 of root canal treating device 100 drives cutting tool 5 with the reverse rotation driving in order to avoid the breakage of cutting tool 5. It should be noted that controller 11 of root canal treating device 100 may stop driving of cutting tool 5 in order to avoid the breakage of cutting tool 5. If controller 11 determines that the load detected by resistor 13*d* for load detection is less than reference load C (NO in step S88), controller 11 keeps the parameters set in step S87 and continues driving of cutting tool 5.

Description has been given to the example in which controller 11 of root canal treating device 100 changes the parameters of the rotation angle and the number of rotations in a stepwise manner and drives cutting tool 5 in steps S81 to S89. The present invention is not, however, limited thereto. Controller 11 may change the parameters of the rotation angle and the number of rotations continuously in accordance with the load applied to cutting tool 5. For example, controller 11 changes the parameter of the normal rotation angle or the reverse rotation angle from 90° to 0° and the parameter of the number of normal rotations or the number of reverse rotations from 400 rpm to 0 rpm continuously in accordance with a change in the load applied to cutting tool 5 from reference load A to reference load C. In addition, the upper limit values of the normal rotation angle and the reverse rotation angle are not limited to 90°. The upper limit values of the number of normal rotations and the number of reverse rotations are not limited to 400 rpm, either.

Description has been given to the case where controller 11 changes only the parameter of the rotation angle in accordance with the load applied to cutting tool 5, the case where controller 11 changes only the parameter of the number of rotations in accordance with the load applied to cutting tool 5, and the case where controller 11 changes both parameters of the rotation angle and the number of rotations in accordance with the load applied to cutting tool 5 in the flowcharts shown in FIGS. 6 to 8. The present invention is not, however, limited thereto.

FIG. 9 is a diagram showing combinations of the parameters that are changed in accordance with the load applied to cutting tool 5. In a setting 1 shown in FIG. 9, controller 11 decreases only the normal rotation angle as the load applied to cutting tool 5 becomes larger. In a setting 2, controller 11 decreases only the number of normal rotations as the load applied to cutting tool 5 becomes larger. In a setting 3, controller 11 decreases the normal rotation angle and the number of normal rotations as the load applied to cutting tool 5 becomes larger.

In a setting 4, controller 11 increases only the reverse rotation angle as the load applied to cutting tool 5 becomes larger. In a setting 5, controller 11 increases only the number of reverse rotations as the load applied to cutting tool 5 becomes larger. In a setting 6, controller 11 increases the reverse rotation angle and the number of reverse rotations as the load applied to cutting tool 5 becomes larger.

In a setting 7 (in the case of the flowchart shown in FIG. 6), controller 11 decreases only the normal rotation angle and increases only the reverse rotation angle as the load applied to cutting tool 5 becomes larger. In a setting 8, controller 11 decreases only the normal rotation angle and increases only the number of reverse rotations as the load applied to cutting tool 5 becomes larger. In a setting 9, controller 11 decreases only the normal rotation angle and increases the reverse rotation angle and the number of reverse rotations as the load applied to cutting tool 5 becomes larger.

In a setting 10, controller 11 decreases only the number of normal rotations and increases only the reverse rotation angle as the load applied to cutting tool 5 becomes larger. In a setting 11 (in the case of the flowchart shown in FIG. 7), controller 11 decreases only the number of normal rotations and increases only the number of reverse rotations as the load applied to cutting tool 5 becomes larger. In a setting 12, controller 11 decreases only the number of normal rotations and increases the reverse rotation angle and the number of reverse rotations as the load applied to cutting tool 5 becomes larger.

In a setting 13, controller 11 decreases the normal rotation angle and the number of normal rotations and increases only the reverse rotation angle as the load applied to cutting tool 5 becomes larger. In a setting 14, controller 11 decreases the normal rotation angle and the number of normal rotations and increases only the number of reverse rotations as the load applied to cutting tool 5 becomes larger. In a setting 15 (in the case of the flowchart shown in FIG. 8), controller 11 decreases the normal rotation angle and the number of normal rotations and increases the reverse rotation angle and the number of reverse rotations as the load applied to cutting tool 5 becomes larger.

In the above description, controller 11 changes at least one parameter of the normal rotation angle and the number of normal rotations such that the parameter becomes smaller as the load applied to cutting tool 5 becomes larger, or changes at least one parameter of the reverse rotation angle and the number of reverse rotations such that the parameter becomes larger as the load applied to cutting tool 5 becomes larger.

Controller 11 may, however, change at least one parameter of the normal rotation angle, the number of normal rotations, the reverse rotation angle, and the number of reverse rotations such that the reverse rotation angle becomes larger than the normal rotation angle as the load applied to cutting tool 5 becomes larger and/or such that the number of reverse rotations becomes larger than the number of normal rotations as the load applied to cutting tool 5 becomes larger. In other words, by changing the parameters as in step S67 shown in FIG. 6 and in step S77 shown in FIG. 7, controller 11 can reduce the load applied to cutting tool 5.

FIG. 10 is a diagram showing a relationship among the parameters that are changed in accordance with the load applied to cutting tool 5. In a setting A shown in FIG. 10, controller 11 changes at least one parameter of the normal rotation angle and the reverse rotation angle such that the reverse rotation angle becomes larger than the normal rotation angle as the load applied to cutting tool 5 becomes larger. For example, when cutting tool 5 is driven with the normal rotation angle being 60° and the reverse rotation angle being 30°, controller 11 may change the normal rotation angle to 20° or may change the reverse rotation angle to 70° or may change the normal rotation angle to 30° and the reverse rotation angle to 70°, as long as the reverse rotation angle becomes larger than the normal rotation angle.

In a setting B, controller 11 changes at least one parameter of the number of normal rotations and the number of reverse rotations such that the number of reverse rotations becomes larger than the number of normal rotations as the load applied to cutting tool 5 becomes larger. For example, when cutting tool 5 is driven with the number of normal rotations being 200 rpm and the number of reverse rotations being 100 rpm, controller 11 may change the number of normal rotations to 100 rpm or may change the number of reverse rotations to 300 rpm or may change the number of normal rotations to 100 rpm and the number of reverse rotations to 300 rpm, as long as the number of reverse rotations becomes larger than the number of normal rotations.

In a setting C, controller 11 changes at least one parameter of the normal rotation angle, the reverse rotation angle, the number of normal rotations, and the number of reverse rotations such that the reverse rotation angle becomes larger than the normal rotation angle as the load applied to cutting tool 5 becomes larger and such that the number of reverse rotations becomes larger than the number of normal rotations as the load applied to cutting tool 5 becomes larger. For example, when cutting tool 5 is driven with the normal rotation angle being 60°, the reverse rotation angle being 30°, the number of normal rotations being 200 rpm, and the number of reverse rotations being 100 rpm, controller 11 may change the normal rotation angle to 20° and the number of normal rotations to 100 rpm or may change the reverse rotation angle to 70° and the number of reverse rotations to 300 rpm or may change the normal rotation angle to 30° and the reverse rotation angle to 70° as well as the number of normal rotations to 100 rpm and the number of reverse rotations to 300 rpm, as long as the reverse rotation angle becomes larger than the normal rotation angle and the number of reverse rotations becomes larger than the number of normal rotations.

As described above, controller 11 of root canal treating device 100 according to the first embodiment of the present invention changes at least one parameter of the normal rotation angle, the number of normal rotations, the reverse rotation angle, and the number of reverse rotations in accordance with the load applied to cutting tool 5, which is detected by resistor 13d for load detection. Therefore, in root canal treating device 100, even in the case of driving cutting tool 5 with the twist driving, the load applied to cutting tool 5 can be reduced to fall within an appropriate range as in the case of driving cutting tool 5 with the normal driving, and the breakage of cutting tool 5 and excessive cutting can be prevented and safe cutting can be achieved.

Description has been given to the case where in root canal treating device 100, cutting tool 5 is driven with the normal rotation driving at the start of driving, and thereafter, driving is switched to the twist driving in the flowcharts shown in FIGS. 6 to 8. The present invention is not, however, limited thereto. Cutting tool 5 may be driven with the twist driving from the start of driving.

In addition, as long as the stress applied to cutting tool 5 can be limited to within the appropriate range, controller 11 may change at least one parameter of the normal rotation angle and the number of normal rotations such that the parameter becomes larger or change at least one parameter of the reverse rotation angle and the number of reverse rotations such that the parameter becomes smaller, when the load applied to cutting tool 5 becomes smaller.

Second Embodiment

In the first embodiment, description has been given to root canal treating device 100 in which at least one parameter of the normal rotation angle, the number of normal rotations, the reverse rotation angle, and the number of reverse rotations is changed in accordance with the load applied to cutting tool 5, which is detected by resistor 13d for load detection. However, the driving state of the cutting tool that is referred to for the purpose of changing the parameters such as the normal rotation angle is not limited to the load applied to cutting tool 5 but may be a position of the tip end of cutting tool 5 in the root canal (hereinafter also simply referred to as the position of cutting tool 5) that is obtained by root canal length measuring circuit 12. In a root canal treating device according to a second embodiment, at least one parameter of the normal rotation angle, the number of normal rotations, the reverse rotation angle, and the number of reverse rotations is changed in accordance with the position of cutting tool 5 obtained by root canal length measuring circuit 12.

Since the root canal treating device according to the second embodiment has the same configuration as that of root canal treating device 100 according to the first embodiment shown in FIGS. 1 to 3, the same reference characters are assigned and detailed description will not be repeated.

Next, description is given to driving of cutting tool 5 of root canal treating device 100 according to the second embodiment. In root canal treating device 100 according to the second embodiment, cutting tool 5 is driven with the normal rotation driving, not the twist driving, at the start of driving, and cutting tool 5 is driven with the twist driving when the position of cutting tool 5 reaches a reference position A (second reference position). After cutting tool 5 is driven with the twist driving, controller 11 of root canal treating device 100 changes at least one parameter of the rotation angle in the normal rotation and the rotation angle speed in the normal rotation such that the parameter becomes smaller as the position of cutting tool 5 changes to reference positions B and C, or changes at least one parameter of the rotation angle in the reverse rotation and the rotation angle speed in the reverse rotation such that the parameter becomes larger as the position of cutting tool 5 changes to reference positions B and C. When the position of cutting tool 5 reaches a reference position D (first reference position), controller 11 of root canal treating device 100 drives cutting tool 5 with the reverse rotation driving or stops driving. The position of cutting tool 5 is located in a direction from the hand piece 1 side toward the root apex in the order of reference position A, reference position B, reference position C, and reference position D.

Figure 11:
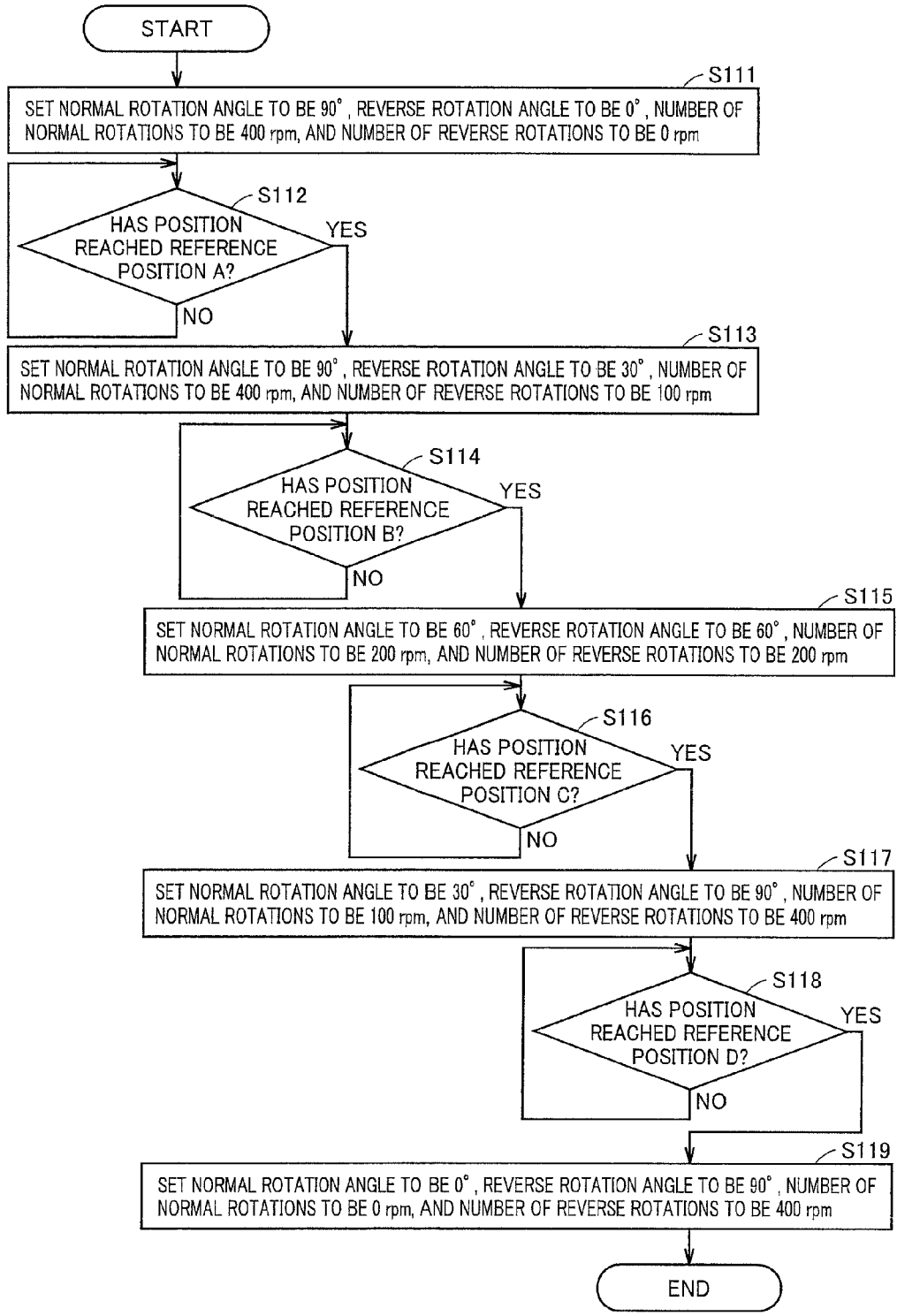
FIG. 11 is a flowchart for describing an example of driving, of a cutting tool of a root canal treating device according to a second embodiment of the present invention.

FIG. 11 is a flowchart for describing an example of driving of cutting tool 5 of root canal treating device 100 according to the second embodiment of the present invention. First, controller 11 sets the normal rotation angle to be 90°, the reverse rotation angle to be 0°, the number of normal rotations to be 400 rpm, and the number of reverse rotations to be 0 rpm, and drives cutting tool 5 (step S111). Since the reverse rotation angle is set to be 0° and the number of reverse rotations is set to be 0 rpm, controller 11 of root canal treating device 100 rotates cutting tool 5 in the normal rotation direction continuously and executes the normal rotation driving.

Next, controller 11 determines whether the position of cutting tool 5 obtained by root canal length measuring circuit 12 has reached reference position A or not (step S112). When the position of cutting tool 5 obtained by root canal length measuring circuit 12 has not yet reached reference position A, controller 11 of root canal treating device 100 drives cutting tool 5 only with the normal rotation driving.

If controller 11 determines that the position of cutting tool 5 obtained by root canal length measuring circuit 12 has reached reference position A (YES in step S112), controller 11 sets the normal rotation angle to be 90°, the reverse rotation angle to be 30°, the number of normal rotations to be 400 rpm, and the number of reverse rotations to be 100 rpm, and drives cutting tool 5 (step S113). In other words, controller 11 of root canal treating device 100 increases the reverse rotation angle from 0° to 30°, increases the number of reverse rotations from 0 rpm to 100 rpm and drives cutting tool 5 with the twist driving such that the load applied to cutting tool 5 falls within the appropriate range in accordance with the position of cutting tool 5. If controller 11 determines that the position of cutting tool 5 obtained by root canal length measuring circuit 12 has not yet reached reference position A (NO in step S112), controller 11 keeps the parameters set in step S111 and continues driving of cutting tool 5.

Next, controller 11 determines whether the position of cutting tool 5 obtained by root canal length, measuring circuit 12 has reached reference position B or not (step S114). Reference position B is located closer to the root apex than reference position A, and the load applied to cutting tool 5 at reference position B is larger than the load applied to cutting tool 5 at reference position A.

If controller 11 determines that the position of cutting tool 5 obtained by root canal length measuring circuit 12 has reached reference position B (YES in step S114), controller 11 sets the normal rotation angle to be 60°, the reverse rotation angle to be 60°, the number of normal rotations to be 200 rpm, and the number of reverse rotations to be 200 rpm, and drives cutting tool 5 (step S115). In other words, controller 11 of root canal treating device 100 decreases the normal rotation angle from 90° to 60°, decreases the number of normal rotations from 400 rpm to 200 rpm, increases the reverse rotation angle from 30° to 60°, increases the number of reverse rotations from 100 rpm to 200 rpm, and drives cutting tool 5 with the twist driving such that the load applied to cutting tool 5 falls within the appropriate range in accordance with the position of cutting tool 5. If controller 11 determines that the position of cutting tool 5 obtained by root canal length measuring circuit 12 has not yet reached reference position B (NO in step S114), controller 11 keeps the parameters set in step S113 and continues driving of cutting tool 5.

Next, controller 11 determines whether the position of cutting tool 5 obtained by root canal length measuring circuit 12 has reached reference position C or not (step S116). Reference position C is located closer to the root apex than reference position B, and the load applied to cutting tool 5 at reference position C is larger than the load applied to cutting tool 5 at reference position B.

If controller 11 determines that the position of cutting tool 5 obtained by root canal length measuring circuit 12 has reached reference position C (YES in step S116), controller 11 sets the normal rotation angle to be 30°, the reverse rotation angle to be 90°, the number of normal rotations to be 100 rpm, and the number of reverse rotations to be 400 rpm, and drives cutting tool 5 (step S117). In other words, controller 11 of root canal treating device 100 decreases the normal rotation angle from 60° to 30°, decreases the number of normal rotations from 200 rpm to 100 rpm, increases the reverse rotation angle from 60° to 90°, increases the number of reverse rotations from 200 rpm to 400 rpm and drives cutting tool 5 with the twist driving such that the load applied to cutting tool 5 falls within the appropriate range in accordance with the position of cutting tool 5. If controller 11 determines that the position of cutting tool 5 obtained by root canal length measuring circuit 12 has not yet reached reference position C (NO in step S116), controller 11 keeps the parameters set in step S115 and continues driving of cutting tool 5.

Next, controller 11 determines whether the position of cutting tool 5 obtained by root canal length measuring circuit 12 has reached reference position D or not (step S118). Reference position D indicates the position of the root apex and is located at the gauge "APEX" shown in FIG. 5. When cutting tool 5 reaches the position of the root apex, controller 11 drives cutting tool 5 such that the root canal is not cut and enlarged any more by reducing the attractive force in the direction of the root apex.

If controller 11 determines that the position of cutting tool 5 obtained by root canal length measuring circuit 12 has reached reference position D (YES in step S118), controller 11 sets the normal rotation angle to be 0°, the reverse rotation angle to be 90°, the number of normal rotations to be 0 rpm, and the number of reverse rotations to be 400 rpm, and drives cutting tool 5 (step S119). Since the normal rotation angle is set to be 0° and the number of normal rotations is set to be 0 rpm, controller 11 of root canal treating device 100 rotates cutting tool 5 in the reverse rotation direction continuously and executes the reverse rotation driving. In other words, controller 11 of root canal treating device 100 drives cutting tool 5 with the reverse rotation driving such that the root canal is not cut and enlarged any more. It should be noted that controller 11 of root canal treating device 100 may stop driving of cutting tool 5 such that the root canal is not cut and enlarged any more. If controller 11 determines that the position of cutting tool 5 obtained by root canal length measuring circuit 12 has not yet reached reference position D (NO in step S118), controller 11 keeps the parameters set in step S117 and continues driving of cutting tool 5.

Description has been given to the example in which controller 11 of root canal treating device 100 changes the parameters of the rotation angle and the number of rotations in a stepwise manner and drives cutting tool 5 in steps S111 to S119. The present invention is not however, limited thereto. Controller 11 may change the parameters of the rotation angle and the number of rotations continuously in accordance with the position of cutting tool 5. For example, controller 11 changes the parameter of the normal rotation angle or the reverse rotation angle from 90° to 0° and the parameter of the number of normal rotations or the number of reverse rotations from 400 rpm to 0 rpm continuously in accordance with a change in the position of cutting tool 5 from reference position A to reference position C. In addition, the upper limit values of the normal rotation angle and the reverse rotation angle are not limited to 90°. The upper limit values of the number of normal rotations and the number of reverse rotations are not limited to 400 rpm, either.

Description has been given to the case where controller 11 changes both parameters of the rotation angle and the number of rotations in accordance with the position of cutting tool 5 in the flowchart shown in FIG. 11. The present invention is not, however, limited thereto. Similarly to the first embodiment, controller 11 of root canal treating device 100 according to the second embodiment may change the parameters as shown in FIGS. 9 and 10 in accordance with the position of cutting tool 5.

As described above, controller 11 of root canal treating device 100 according to the second embodiment of the present invention changes at least one parameter of the normal rotation angle, the number of normal rotations, the reverse rotation angle, and the number of reverse rotations in accordance with the position of cutting tool 5 obtained by root canal length measuring circuit 12. Therefore, in root canal treating device 100 according to the second embodiment of the present invention, even in the case of driving cutting tool 5 with the twist driving, the load applied to cutting tool 5 can be reduced to fall within the appropriate range as in the case of driving cutting tool with the normal driving, and the breakage of cutting tool 5 and excessive cutting can be prevented. Furthermore, in root canal treating device 100 according to the second embodiment of the present invention, safe cutting can be achieved by reducing the attractive force in the direction of the root apex as cutting tool 5 comes closer to the root apex.

Third Embodiment

A combination of the load applied to cutting tool 5 and the position of cutting tool 5 may be used as the driving state of the cutting tool that is referred to for the purpose of changing the parameters such as the normal rotation angle. In a root canal treating device according to a third embodiment, at least one parameter of the normal rotation angle, the number of normal rotations, the reverse rotation angle, and the number of reverse rotations is changed in accordance with the load applied to cutting tool 5, which is detected by resistor 13d for load detection, and the position of cutting tool 5 obtained by root canal length measuring circuit 12.

Since the root canal treating device according to the third embodiment has the same configuration as that of root canal treating device 100 according to the first embodiment shown in FIGS. 1 to 3, the same reference characters are assigned and detailed description will not be repeated.

Next, description is given to driving of cutting tool 5 of root canal treating device 100 according to the third embodiment. In root canal treating device 100 according to the third embodiment, cutting tool 5 is driven with the normal rotation driving, not the twist driving, at the start of driving, and cutting tool 5 is driven with the twist driving when the load applied to cutting tool 5 becomes equal to or larger than reference load A (second reference load) or when the position of cutting tool 5 reaches reference position A (second reference position). After cutting tool 5 is driven with the twist driving, controller 11 of root canal treating device 100 changes at least one parameter of the rotation angle in the normal rotation and the rotation angle speed in the normal rotation such that the parameter becomes smaller as the load becomes larger, or changes at least one parameter of the rotation angle in the reverse rotation and the rotation angle speed in the reverse rotation such that the parameter becomes larger as the load becomes larger, in order that the load applied to cutting tool 5 becomes equal to or smaller than reference load B. When the load applied to cutting tool 5 becomes equal to or larger than reference load C (first reference load) or when the position of cutting tool 5 reaches reference position D (first reference position), controller 11 of root canal treating device 100 drives cutting tool 5 with the reverse rotation driving or stops driving.

Figure 12:
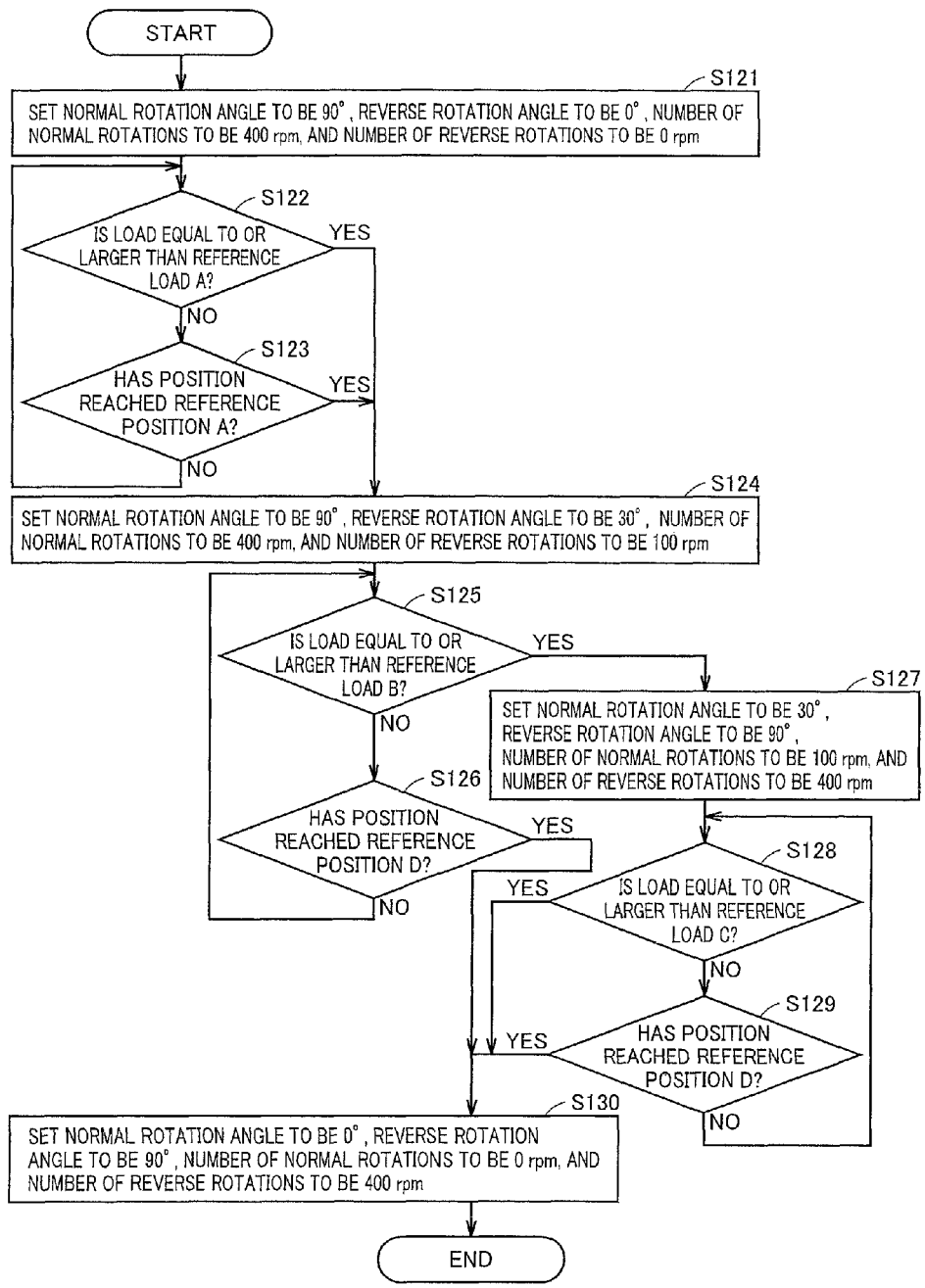
FIG. 12 is a flowchart for describing an example of driving of a cutting tool of a root canal treating device according to a third embodiment of the present invention.

FIG. 12 is a flowchart for describing an example of driving of cutting tool 5 of root canal treating device 100 according to the third embodiment of the present invention. First, controller 11 sets the normal rotation angle to be 90°, the reverse rotation angle to be 0°, the number of normal rotations to be 400 rpm, and the number of reverse rotations to be 0 rpm, and drives cutting tool 5 (step S121). Since the reverse rotation angle is set to be 0° and the number of reverse rotations is set to be 0 rpm, controller 11 of root canal treating device 100 rotates cutting tool 5 in the normal rotation direction continuously and executes the normal rotation driving.

Next, controller 11 determines whether or not the load detected by resistor 13d for load detection is equal to or larger than reference load A (step S122).

If controller 11 determines that the load detected by resistor 13d for load detection is equal to or larger than reference load A (YES in step S122), controller 11 sets the normal rotation angle to be 90°, the reverse rotation angle to be 30°, the number of normal rotations to be 400 rpm, and the number of reverse rotations to be 100 rpm, and drives cutting tool 5 (step S124). In other words, controller 11 of root canal treating device 100 increases the reverse rotation angle from 0° to 30°, increases the number of reverse rotations from 0 rpm to 100 rpm and drives cutting tool 5 with the twist driving such that the load applied to cutting tool 5 falls within the appropriate range.

If controller 11 determines that the load detected by resistor 13d for load detection is less than reference load A (NO in step S122), controller 11 determines whether the position of cutting tool 5 obtained by root canal length measuring circuit 12 has reached reference position A or not (step S123).

If controller 11 determines that the position of cutting tool 5 obtained by root canal length measuring circuit 12 has reached reference position A (YES in step S123), controller 11 sets the normal rotation angle to be 90°, the reverse rotation angle to be 30°, the number of normal rotations to be 400 rpm, and the number of reverse rotations to be 100 rpm, and drives cutting tool 5 (step S124). If controller 11 determines that the position of cutting tool 5 obtained by root canal length measuring circuit 12 has not yet reached reference position A (NO in step S123), controller 11 keeps the parameters set in step S121 and continues driving of cutting tool 5.

Next, controller 11 determines whether or not the load detected by resistor 13d for load detection is equal to or larger than reference load B (step S125).

If controller 11 determines that the load detected by resistor 13d for load detection is equal to or larger than reference load B (YES in step S125), controller 11 sets the normal rotation angle to be 30°, the reverse rotation angle to be 90°, the number of normal rotations to be 100 rpm, and the number of reverse rotations to be 400 rpm, and drives cutting tool 5 (step S127). In other words, controller 11 of root canal treating device 100 decreases the normal rotation angle from 90° to 30°, decreases the number of normal rotations from 400 rpm to 100 rpm, increases the reverse rotation angle from 30° to 90°, increases the number of reverse rotations from 100 rpm to 400 rpm, and drives cutting tool 5 with the twist driving such that the load applied to cutting tool 5 falls within the appropriate range.

If controller 11 determines that the load detected by resistor 13d for load detection is less than reference load B (NO in step S125), controller 11 determines whether the position of cutting tool 5 obtained by root canal length measuring circuit 12 has reached reference position D or not (step S126).

If controller 11 determines that the position of cutting tool 5 obtained by root canal length measuring circuit 12 has reached reference position D (YES in step S126), controller 11 sets the normal rotation angle to be 0°, the reverse rotation angle to be 90°, the number of normal rotations to be 0 rpm, and the number of reverse rotations to be 400 rpm, and drives cutting tool 5 (step S130). Since the normal rotation angle is set to be 0° and the number of normal rotations is set to be 0 rpm, controller 11 of root canal treating device 100 drives cutting tool 5 in the reverse rotation direction continuously and executes the reverse rotation driving. In other words, controller 11 of root canal treating device 100 drives cutting tool 5 with the reverse rotation driving such that the root canal is not cut and enlarged any more. It should be noted that controller 11 of root canal treating device 100 may stop driving of cutting tool 5 such that the root canal is not cut and enlarged any more. If controller 11 determines that the position of cutting tool 5 obtained by root canal length measuring circuit 12 has not yet reached reference position D (NO in step S126), controller 11 keeps the parameters set in step S124 and continues driving of cutting tool 5.

After controller 11 determines that the load detected by resistor 13d for load detection is equal to or larger than reference load B (YES in step S125) and sets the normal rotation angle to be 30°, the reverse rotation angle to be 90°, the number of normal rotations to be 100 rpm, and the number of reverse rotations to be 400 rpm (step S127), controller 11 determines whether or not the load detected by resistor 13d for load detection is equal to or larger than reference load C (step S128). When the load applied to cutting tool 5 is equal to or larger than reference load C even if the parameters are changed and cutting tool 5 is driven, controller 11 executes driving for avoiding the breakage of cutting tool 5.

If controller 11 determines that the load detected by resistor 13d for load detection is equal to or larger than reference load C (YES in step S128), controller 11 sets the normal rotation angle to be 0°, the reverse rotation angle to be 90°, the number of normal rotations to be 0 rpm, and the number of reverse rotations to be 400 rpm, and drives cutting tool 5 (step S130). If controller 11 determines that the load detected by resistor 13d for load detection is less than reference load C (NO in step S128), controller 11 determines whether the position of cutting tool 5 obtained by root canal length measuring circuit 12 has reached reference position D or not (step S129).

If controller 11 determines that the position of cutting tool 5 obtained by root canal length measuring circuit 12 has reached reference position D (YES in step S129), controller 11 sets the normal rotation angle to be 0°, the reverse rotation angle to be 90°, the number of normal rotations to be 0 rpm, and the number of reverse rotations to be 400 rpm, and drives cutting tool 5 (step S130). If controller 11 determines that the position of cutting tool 5 obtained by root canal length measuring circuit 12 has not yet reached reference position D (NO in step S129), controller 11 keeps the parameters set in step S127 and continues driving of cutting tool 5.

Description has been given to the example in which controller 11 of root canal treating device 100 changes the parameters of the rotation angle and the number of rotations in a stepwise manner and drives cutting tool 5 in steps S121 to S130. The present invention is not, however, limited thereto. Controller 11 may change the parameters of the rotation angle and the number of rotations continuously in accordance with the position of cutting tool 5. For example, controller 11 changes the parameter of the normal rotation angle or the reverse rotation angle from 90° to 0° and the parameter of the number of normal rotations or the number of reverse rotations from 400 rpm to 0 rpm continuously in accordance with a change in the load applied to cutting tool 5 from reference load A to reference load C or a change in the position of cutting tool 5 from reference position A to reference position D. In addition, the upper limit values of the normal rotation angle and the reverse rotation angle are not limited to 90°. The upper limit values of the number of normal rotations and the number of reverse rotations are not limited to 400 rpm, either.

Description has been given to the case where controller 11 changes both parameters of the rotation angle and the number of rotations in accordance with the load applied to cutting tool 5 or the position of cutting tool 5 in the flowchart shown in FIG. 12. The present invention is not, however, limited thereto. Similarly to the first embodiment, controller 11 of root canal treating device 100 according to the third embodiment may change the parameters as shown in FIGS. 9 and 10 in accordance with the load applied to cutting tool 5 or the position of cutting tool 5.

As described above, controller 11 of root canal treating device 100 according to the third embodiment of the present invention changes at least one parameter of the normal rotation angle, the number of normal rotations, the reverse rotation angle, and the number of reverse rotations in accordance with the load detected by resistor 13d for load detection or the position of cutting tool 5 obtained by root canal length measuring circuit 12. Therefore, in root canal treating device 100 according to the third embodiment of the present invention, even in the case of driving cutting tool 5 with the twist driving, the load applied to cutting tool 5 can be reduced to fall within the appropriate range as in the case of driving cutting tool 5 with the normal driving, and the breakage of cutting tool 5 and excessive cutting can be prevented. Furthermore, in root canal treating device 100 according to the third embodiment of the present invention, safe cutting can be achieved by reducing the attractive force in the direction of the root apex as cutting tool 5 comes closer to the root apex.

Figure 13:
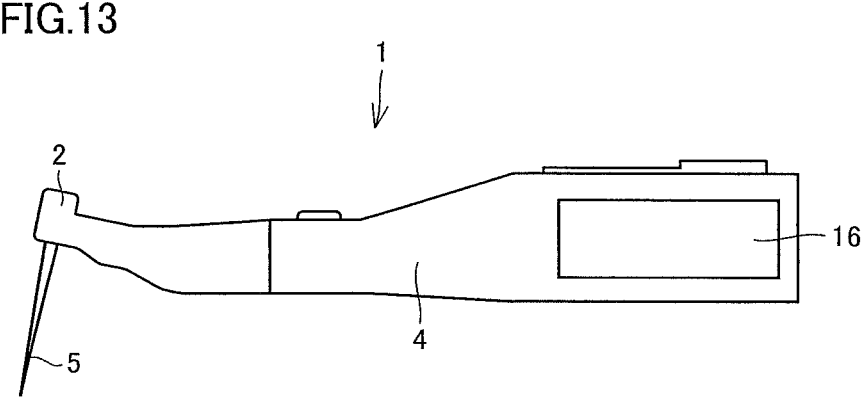
FIG. 13 is a schematic diagram showing a configuration of a cordless-type root canal treating device.

In root canal treating device 100 according to the first to third embodiments, the configuration in which hand piece 1 is coupled to control box 9 via hose 61 has been described. The present invention is not, however, limited thereto but may be configured as a cordless-type root canal treating device. FIG. 13 is a schematic diagram showing a configuration of the cordless-type root canal treating device. In the cordless-type root canal treating device shown in FIG. 13, a battery pack, a micro motor, and a control system corresponding to a control box are incorporated into grip 4 of hand piece 1, and each type of operation units is disposed on a surface of grip 4. Furthermore, in the cordless-type root canal treating device, grip 4 is provided with display unit 16. Therefore, the user can check information such as whether cutting tool 5 is being driven with the normal driving or with the twist driving, where the current position of cutting tool 5 is, how much load is being applied to cutting tool 5, and what is the number of rotations, without significantly changing a user's line of sight. Although not shown, lead 19 for mouth electrode 19a may be configured to be led from grip 4.

In addition, in root canal treating device 100 according to the first to third embodiments, the case where micro motor 7 is used as a power source for driving cutting tool 5 has been described. The present invention is not, however, limited thereto. Another driving source such as an air turbine may be used.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A dental treating apparatus, comprising:
   a hand piece for drivably holding a cutting tool on a head unit;
   a power source for driving said cutting tool;
   a driving unit for, when a rotation direction in which said cutting tool cuts an object to be cut is defined as normal rotation and a rotation direction opposite to said normal rotation is defined as reverse rotation, driving said cutting tool with twist driving from a start of driving, wherein the twist driving comprises said normal rotation and said reverse rotation being repeated;
   a driving state detecting unit for detecting a driving state of said cutting tool,
   wherein the start of driving is a timing before detecting the driving state of said cutting tool by the driving state detecting unit; and
   a controller for changing at least one parameter from the group consisting of a rotation angle in said normal rotation, a rotation angle speed in said normal rotation, a rotation angle in said reverse rotation, and a rotation angle speed in said reverse rotation,
      such that the rotation angle in said reverse rotation becomes larger than the rotation angle in said normal rotation in accordance with said driving state of said cutting tool detected by said driving state detecting unit if the rotation angle in said normal rotation is larger than the rotation angle in said reverse rotation from the start of driving, or
      such that the rotation angle speed in said reverse rotation becomes larger than the rotation angle speed in said normal rotation in accordance with said driving state of said cutting tool detected by said driving state detecting unit if the rotation angle speed in said normal rotation is larger than the rotation angle speed in said reverse rotation from the start of driving.

2. The dental treating apparatus according to claim 1,
   wherein said driving state detecting unit detects a load applied to said cutting tool at a time of driving as said driving state of said cutting tool, and
   wherein said controller changes said at least one parameter in accordance with said load detected by said driving state detecting unit.

3. The dental treating apparatus according to claim 2,
   wherein said controller changes at least one of the rotation angle in said normal rotation and the rotation angle speed in said normal rotation to become smaller as said load detected by said driving state detecting unit becomes larger, or changes at least one of the rotation angle in said reverse rotation and the rotation angle speed in said reverse rotation to become larger as said load detected by said driving state detecting unit becomes larger.

4. The dental treating apparatus according to claim 2,
   wherein said controller changes said at least one parameter such that the rotation angle in said reverse rotation becomes larger than the rotation angle in said normal rotation as said load detected by said driving state detecting unit becomes larger and/or such that the rotation angle speed in said reverse rotation becomes larger than the rotation angle speed in said normal rotation as said load detected by said driving state detecting unit becomes larger.

5. The dental treating apparatus according to claim 2,
   wherein said controller changes said at least one parameter such that said driving unit drives said cutting tool only with said reverse rotation driving or stops driving when said load detected by said driving state detecting unit is equal to or larger than a predetermined first reference load, and
   wherein said controller changes said at least one parameter such that said driving unit drives said cutting tool only with said normal rotation driving when said load detected by said driving state detecting unit is less than a second reference load smaller than said first reference load.

6. The dental treating apparatus according to claim 1,
   wherein said driving state detecting unit detects a position of a tip end of said cutting tool in a root canal obtained by electrical root canal length measurement as said driving state of said cutting tool, and
   wherein said controller changes said at least one parameter in accordance with said position detected by said driving state detecting unit.

7. The dental treating apparatus according to claim 6, wherein
   said controller changes at least one of the rotation angle in said normal rotation and the rotation angle speed in said normal rotation to become smaller as said position detected by said driving state detecting unit comes closer to a predetermined first reference position, or changes at least one of the rotation angle in said reverse rotation and the rotation angle speed in said reverse rotation to become larger as said position detected by said driving state detecting unit comes closer to the predetermined first reference position.

8. The dental treating apparatus according to claim 6, wherein
    said controller changes said at least one parameter,
    such that the rotation angle in said reverse rotation becomes larger than the rotation angle in said normal rotation also as said position detected by said driving state detecting unit comes closer to a predetermined first reference position, and/or
    such that the rotation angle speed in said reverse rotation becomes larger than the rotation angle speed in said normal rotation also as said position detected by said driving state detecting unit comes closer to the predetermined first reference position.

9. The dental treating apparatus according to claim 6,
    wherein said controller changes said at least one parameter such that said driving unit drives said cutting tool only with said reverse rotation driving or stops driving when said position detected by said driving state detecting unit reaches a predetermined first reference position, and
    wherein said controller changes said at least one parameter such that said driving unit drives said cutting tool only with said normal rotation driving when said position detected by said driving state detecting unit does not reach a second reference position located closer to said hand piece than said first reference position.

10. The dental treating apparatus according to claim 1, further comprising:
    a notifier for notifying a user that said controller has changed said at least one parameter.

11. The dental treating apparatus according to claim 10, wherein
    said notifier is a display unit and is provided at said hand piece.

12. The dental treating apparatus according to claim 1, wherein
    said power source is an electrically-driven motor.

13. A method for operating a dental cutting tool during cutting and enlarging an inner wall of a root canal of a tooth, comprising:
    driving the cutting tool with twist driving from a start of driving in which a normal rotation and a reverse rotation are repeated, wherein a rotation direction in which said cutting tool cuts an object to be cut is defined as the normal rotation and a rotation direction opposite to said normal rotation is defined as the reverse rotation;
    detecting a driving state of the cutting tool,
    wherein the start of driving is a timing before detecting the driving state of said cutting tool; and
    controlling at least one parameter from the group consisting of a rotation angle in the normal rotation, a rotation angle speed in the normal rotation, a rotation angle in the reverse rotation, and a rotation angle speed in the reverse rotation,
    such that the rotation angle in the reverse rotation becomes larger than the rotation angle in the normal rotation in accordance with the detected driving state of the cutting tool if the rotation angle in said normal rotation is larger than the rotation angle in said reverse rotation from the start of driving, or
    such that the rotation angle speed in the reverse rotation becomes larger than the rotation angle speed in the normal rotation in accordance with the detected driving state of the cutting tool if the rotation angle speed in said normal rotation is larger than the rotation angle speed in said reverse direction from the start of driving.

* * * * *